United States Patent [19]

DiNinno et al.

[11] Patent Number: 5,192,758

[45] Date of Patent: Mar. 9, 1993

[54] 2-BIPHENYL-CARBAPENEM ANTIBACTERIAL AGENTS

[75] Inventors: Frank DiNinno, Old Bridge; Kevin D. Dykstra, Hewitt; James V. Heck, Scotch Plains, all of N.J.

[73] Assignee: Merck & Co., Inc., Rahway, N.J.

[21] Appl. No.: 843,139

[22] Filed: Feb. 28, 1992

[51] Int. Cl.$^5$ .................. A01N 43/00; A61K 31/395; C07D 487/00
[52] U.S. Cl. ..................... 514/210; 540/302
[58] Field of Search .................. 540/302; 514/210

[56] References Cited

U.S. PATENT DOCUMENTS

| 5,011,832 | 4/1991 | DiNinno et al. | 514/210 |
| 5,025,006 | 6/1991 | DiNinno et al. | 514/210 |

*Primary Examiner*—Marianne M. Cintins
*Assistant Examiner*—Rebecca Cook

*Attorney, Agent, or Firm*—Curtis Panzer; Richard C. Billups; Hesna J. Pfeiffer

[57] ABSTRACT

Carbapenems of the formula

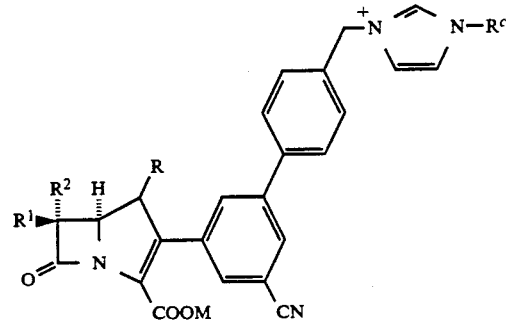

are useful antibacterial agents.

14 Claims, No Drawings

2-BIPHENYL-CARBAPENEM ANTIBACTERIAL AGENTS

BACKGROUND OF THE INVENTION

The present invention relates to antibacterial agents of the carbapenem class, in which the 2-position sidechain is characterized by a biphenyl moiety, substituted by specific cationic and neutral substituents, as described in more detail further below.

Thienamycin was an early carbapenem antibacteiral agent having a broad spectrum; it has the following formula:

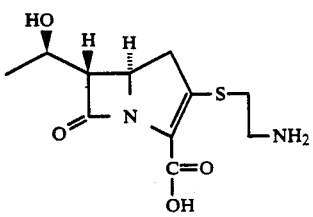

Later, N-formimidoyl thienamycin was discovered; it has the formula:

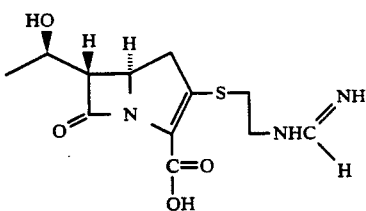

More recently, U.S. Pat. No. 5,025,006 disclosed 2-biphenyl carbapenems of the formula:

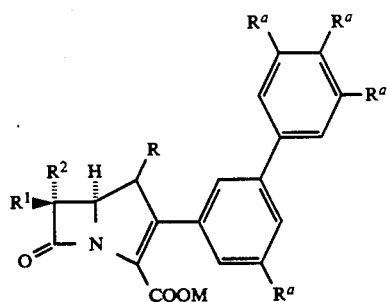

where $R^a$ is broadly classified as a neutral organic substituent. These compounds were found to be effective antibiotics.

Also, U.S. Pat. No. 5,011,832 disclosed 2-biphenyl carbapenems of the immediately above Formula where one of the $R^a$ substituents contains a quaternizeable nitrogen. These compounds were also found to be effective antibiotics.

As a class, the 2-biphenyl-carbapenems are not only of interest for a broad antibacterial spectrum such as that of thienamycin or N-formimidoyl thienamycin. Rather, their spectrum of activity of special interest is to gram positive microorganisms, especially methicillin resistant *Staphyloccus aureus* (MRSA). methicillin resistant *Staphyloccus epidermidis* (MRSE), and methicillin resistant coagulase negative *Staphylococci* (MRCNS). The 2-biphenyl carbapenems thus comprise an important contribution to therapy of these difficult to control pathogens. Within the class of 2-biphenyl carbapenems, there have been new found compounds having an unexpected level of safety. These compounds, to a surprising degree, have low seizure potential.

SUMMARY OF INVENTION

The present invention provides novel carbapenem compounds of the formula:

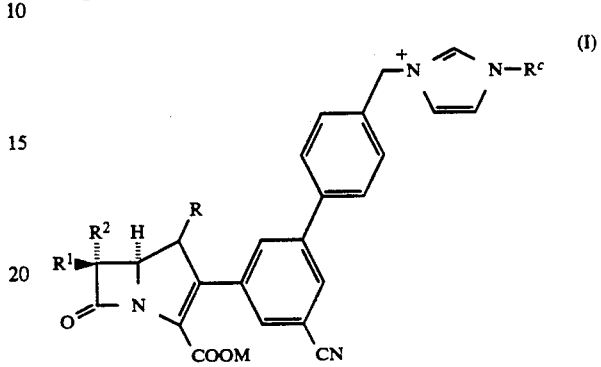

wherein:

R is H or $CH_3$;

$R^1$ and $R^2$ are independently H, $CH_3$—, $CH_3CH_2$—, $(CH_3)_2CH$—, $HOCH_2$—, $CH_3CH(OH)$—, $(CH_3)_2C(OH)$—, $FCH_2CH(OH)$—, $F_2CHCH(OH)$—, $F_3CCH(OH)$—, $CH_3CH(F)$—, $CH_3CF_2$—, or $(CH_3)_2C(F)$—;

$R^c$ is selected from the group consisting of —$CF_3$, and $C_{1-6}$ alkyl where the $C_{1-6}$ alkyl may be mono-substituted with a substituent selected from the group consisting of:

a) a trifluoromethyl group: —$CF_3$;

b) a halogen atom: —Br, —Cl, —F, or —I;

c) $C_{1-4}$ alkoxy radical: —$OC_{1-4}$ alkyl, wherein the alkyl is optionally mono-substituted by $R^q$, where $R^q$ is a member selected from the group consisting of OH, —$OCH_3$, —CN, —$C(O)NH_2$, $OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$ and —$COOC_{1-4}$alkyl;

d) a hydroxy group: —OH;

e) a carbonyloxy radical: —O(C=O)$R^s$, where $R^s$ is $C_{1-4}$ alkyl or phenyl, each of which is optionally mono-substituted by $R^q$ as defined above;

f) a carbamoyloxy radical: —O(C=O)N($R^y$)$R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —S(O)$_2$—, to form a ring (where the ring is optionally mono-substituted with $R^q$ as defined above);

g) a sulfur radical: —S(O)$_n$—$R^s$ where n=0–2, and $R^s$ is defined above;

h) a sulfamoyl group: —$SO_2N(R^y)R^z$ where $R^y$ and $R^z$ are as defined above;

i) azido; $N_3$ j) a formamido group: —N($R^t$)(C=O)H, where $R^t$ is H or $C_{1-4}$ alkyl, and the alkyl thereof is optionally mono-substituted by $R^q$ as defined above;

k) a ($C_{1-4}$ alkyl)carbonylamino radical: —N($R^t$)(-C=O)$C_{1-4}$ alkyl, where $R^t$ is as defined above, and the alkyl group is also optionally mono-substituted by $R^q$ as defined above;

l) a ($C_1$–$C_4$ alkoxy) carbonylamino radical: —N($R^t$)(C=O)O$C_{1-4}$ alkyl, where $R^t$ is as defined above, and the alkyl group is also optionally mono-substituted by $R^q$ as defined above;

m) a ureido group: —N($R^t$)(C=O)N($R^y$)—$R^z$ where $R^t$, $R^y$ and $R^z$ are as defined above;

n) a sulfonamido group: —N($R^t$)SO$_2R^s$, where $R^s$ and $R^t$ are as defined above;

o) a cyano group: —CN;

p) a formyl or acetalized formyl radical: —(C=O)H or —CH(OCH$_3$)$_2$;

q) ($C_1$–$C_4$ alkyl)carbonyl radical wherein the carbonyl is acetalized: —C(OCH$_3$)$_2$$C_{1-4}$ alkyl, where the alkyl is optionally mono-substituted by $R^q$ as defined above;

r) carbonyl radical: —(C=O)$R^s$, where $R^s$ is as defined above;

s) a hydroximinomethyl radical in which the oxygen or carbon atom is optionally substituted by a $C_1$–$C_4$ alkyl group: —(C=NOR$^z$)$R^y$ where $R^y$ and $R^z$ are as defined above, except they may not be joined together to form a ring;

t) a ($C_1$–$C_4$ alkoxy)carbonyl radical: —(C=O)O$C_{1-4}$ alkyl, where the alkyl is optionally mono-substituted by $R^q$ as defined above;

u) a carbamoyl radical: —(C=O)N($R^y$)$R^z$ where $R^y$ and $R^z$ are as defined above;

v) an N-hydroxycarbamoyl or N($C_1$–$C_4$ alkoxy)carbamoyl radical in which the nitrogen atom may be additionally substituted by a $C_1$–$C_4$ alkyl group: —(C=O)—N(OR$^y$)$R^z$ where $R^y$ and $R^z$ are as defined above, except they may not be joined together to form a ring;

w) a thiocarbamoyl group: —(C=S)N($R^y$)($R^z$) where $R^y$ and $R^z$ are as defined above;

y) trifluoromethylthio: —SCF$_3$;

z) $C_5$–$C_7$ cycloalkyl group in which one of the carbon atoms in the ring is replaced by a heteroatom selected from O, S, NH or N($C_1$–$C_4$ alkyl) and in which one additional carbon atom may be replaced by NH or N($C_1$–$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

aa) N$R^y$$R^z$(where $R^y$ and $R^z$ are defined above);

ab) $C_2$–$C_4$ alkenyl radical;

aC) $C_2$–$C_4$ alkynyl radical;

ad) a 2-oxazolidinonyl moiety in which the point of attachment is the nitrogen atom of the oxazolidinone ring, the ring oxygen atom is optionally replaced by a heteroatom selected from —S— and >N$R^t$ (where $R^t$ is as defined above) and one of the saturated carbon atoms of the oxazolidinone ring is optionally mono-substituted by one of the substituents a) to ac) above;

M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

DETAILED DESCRIPTION OF THE INVENTION

The manufacture of compounds of Formula I may be carried out according to various strategies. Basically, there are five tasks that are required to produce these compounds. The base carbapenem or its immediate precursor must be separately constructed. The base biphenyl must be separately made. The biphenyl must be added to the carbapenem. The imidazolium moiety must be substituted on the biphenyl. Lastly, the substituent $R^c$ must be added to the imidazolium or imidazole. A skilled practitioner will recognize that there are several practical sequences in which these tasks may be arranged. In one sequence, $R^c$ may be added to imidazole which is subsequently added to biphenyl, which unit is subsequently added to carbapenem. In another sequence, base biphenyl is added to carbapenem which is followed by the addition of the imidazolium moiety and finally $R^c$.

The preferred sequence herein is one in which base biphenyl is added to carbapenem to form one reactant and $R^c$ is added to imidazole to form a second reactant. The two reactants just described are subsequently reacted to make the final product of Formula I, in protected form of course. A detailed description of this preferred sequence may be divided into four synthetic stages. In the first synthetic stage, there will be described the manufacture of the base biphenyl with precursor substituents as necessary. In the second synthetic stage, there will be described the substitution of the base biphenyl onto the 2-position of carbapenem. In the third synthetic stage, alternative reactions will be taught to substitute imidazole with $R^c$. In the fourth and final synthetic stage, alternative reactions will be taught to substitute the 2-biphenyl moiety the imidazole unit.

In practice, the objective of the first synthetic stage of the suggested sequence is to produce a biphenyl starting material for the second synthetic stage. As Flow Sheets B and C teach alternative processes for the second synthetic stage, it is therefore an object of the first synthetic stage to produce biphenyl starting materials for these Flow Sheets. The desired biphenyl starting material or base biphenyl, as used herein, is 3-bromo-4'hydroxymethyl biphenyl with a 5-position substituent that is cyano or a precursor substituent therefor. In the case of Flow Sheet B, the 5-cyano substituent on the base biphenyl starting material must be in the form of a precursor to cyano that is stable to the reaction conditions.

Flow Sheet A1 demonstrates the manufacture of a biphenyl starting material for Flow Sheet B.

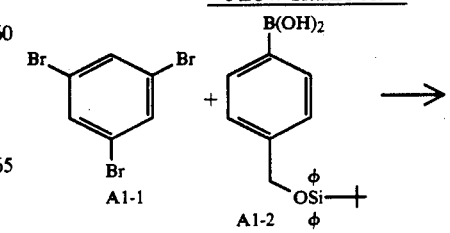

-continued
FLOW SHEET A1

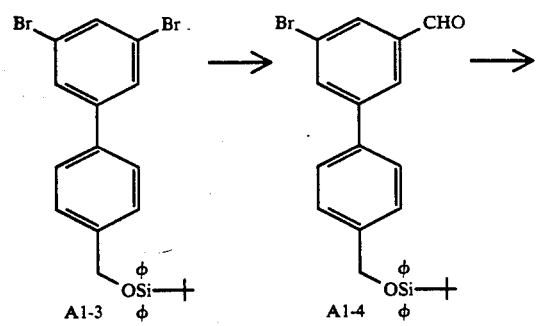

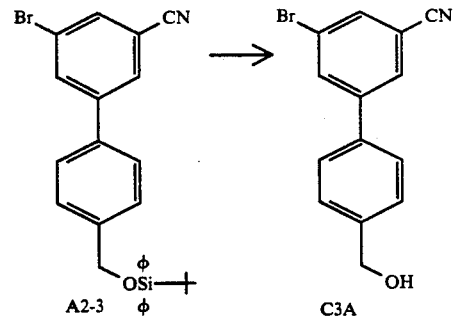

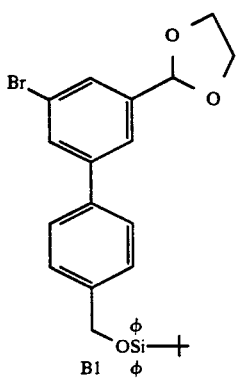

In Flow Sheet A1, a Suzuki reaction is employed to produce biphenyl A1-3 from easily produced starting materials A1-1 and A1-2. In the Suzuki reaction A1-1 is reacted with A1-2 in toluene and aqueous sodium carbonate with (Ph$_3$P)$_4$Pd at from 80°–120° C. The Suzuki reaction is well known in the art and may be found generally described by N. Miyaura, T. Yanagi and A. Suzuki, Syn. Comm., 11, 513 (1981). Subsequently, the 5-bromo biphenyl A1-3 is lithiated in an organic solvent, such as, THF, at −78° C. using n-butyllithium and then formylated with DMF to produce the 5-formyl biphenyl A1-4. Finally, compound A1-4 is heated in benzene with ethylene glycol and p-TsOH to produce the 5-acetal biphenyl B1. Compound B1 is a suitable starting material for Flow Sheet B with the 5-acetal being the precursor substituent for 5-cyano.

Flow Sheet A2 demonstrates the manufacture of a base biphenyl starting material for Flow Sheet C.

FLOW SHEET A2

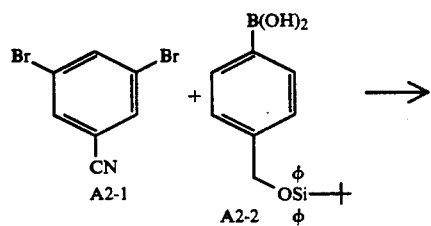

In Flow Sheet A2, a Suzuki reaction is again employed to produce biphenyl A2-3 from starting materials A2-1 and A2-2. The Suzuki reaction is described above in relation to Flow Sheet A1. Biphenyl A2-3 is produced with the 5-cyano substituent as such and need only be deprotected to produce biphenyl C3A, the starting material for Flow Sheet A2. The necessary deprotection is described in detail below.

As stated above, the second stage synthesis is to attach the base biphenyl B1 or C3A to the 2-position of the carbapenem. Biphenyl B1 may be added to azetidin-2-one B2 in a Grignard reaction as shown in Flow Sheet B. The Grignard reaction requires that B1 be converted to a Grignard reagent by reaction with magnesium and 1,2-dibromoethane in THF from 20° C. to 60° C. and subsequently contacting B1 as a Grignard reagent with B2 in THF at from −70° C. to about 20° C. to produce azetidin-2-one B3. Alternatively, B1 may be reacted with t-butyllithium, n-butyllithium, or the like in THF at from −78° C. to −50° C. followed by the addition of magnesium bromide to produce the same Grignard reagent. $R^i$ of B2 is in practice pyrid-2-yl but may clearly be a variety of substituents including aromatic and heteroaromatic substituents. Further $R^i$ might be for example phenyl, pyrimidinyl or thiazolyl.

Azetidin-2-one B3 is an intermediate that may be ring closed to a carbapenem. Prior to closing the ring to carbapenem, however, it is advantageous in terms of yield to replace the 5-acetal on the biphenyl with 5-cyano and to deprotect the 4'-hydroxymethyl of the same biphenyl moiety. Replacing the 5-acetal is a three step process that utilizes a 5-formyl and 5-oxime intermediate to 5-cyano. In a first step, B3 is exposed to HCl with optional heating to form an equivalent 5-formyl compound. In the second step, the 5-formyl compound is reacted with hydroxylamine hydrochloride in pyridine and ethanol at about 0° C. to produce the equivalent 5-oxime compound. In the third step, the 5-oxime compound is reacted with triflic anhydride in CH$_2$Cl$_2$ at −78° C. to room temperature in the presence of triethylamine to produce the 5-cyano B4. Deprotecting the 4'-hydroxymethyl is conveniently done by exposing compound B4 to a 2% dilute solution of sulfuric acid in methanol at 0° C. for from a few minutes to several hours to produce compound B5. If the t-butyldiphenylsilyl group was removed under the same conditions after cyclization of B4 to carbapenem, a substantial portion of the carbapenem would be degraded and lost. As the last step of Flow Sheet B, the ring of B5 is closed to produce 2-base biphenyl carbapenem. In this ring closure reaction, B5 is refluxed in xylene with a trace of p-hydroquinone for about 1 to 2 hours in an inert atmosphere to produce compound B6.

FLOW SHEET B

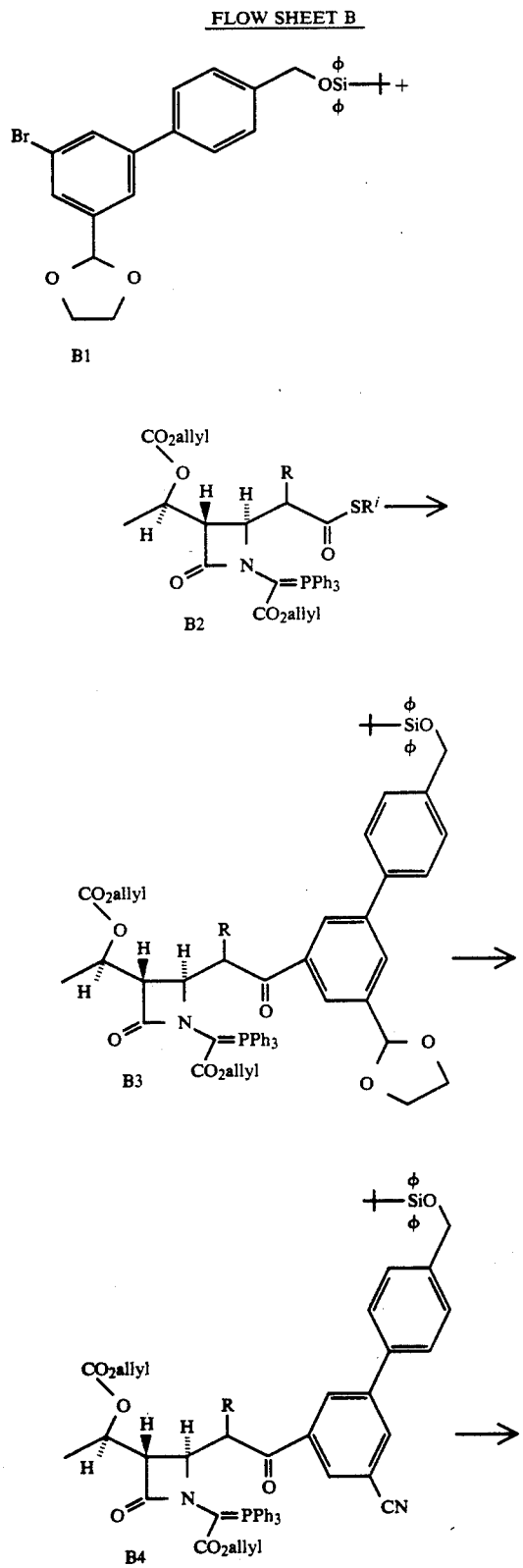

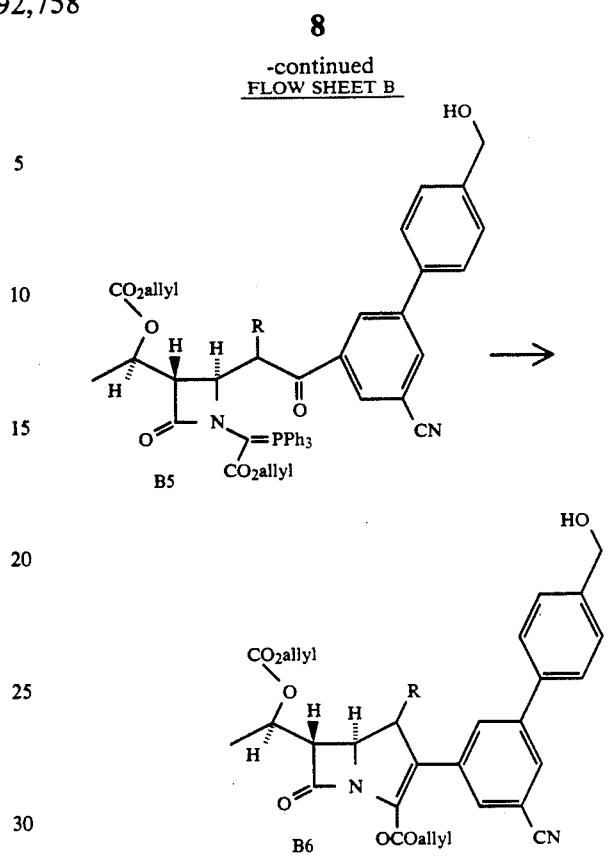

Flow Sheet C shows an alternative second stage synthesis, i.e. attachment of the base biphenyl such as C3A to the 2-position of the carbapenem. This synthesis involves a palladium catalyzed cross-coupling reaction between a carbapenem triflate and a suitably substituted arylstannane, a process which is described in U.S. patent application Ser. No. 485,096 filed Feb. 26, 1990, hereby incorporated by reference. In order to apply this synthesis, it is first necessary to modify bromobiphenyl C3A to the trimethylstannylbiphenyl C3. This is accomplished by simply heating C3A with hexamethylditin in the presence of tetrakistriphenylphosphinepalladium in toluene solution. Referring again to Flow Sheet C, the 2-oxocarbapenam C1 is reacted with a suitable trifluoromethanesulfonyl source, such as trifluoromethanesulfonic anhydride. trifluoromethanesulfonyl chloride and the like, in the presence of an organic nitrogen base, such as triethylamine, diisopropylamine and the like, in polar aprotic solvent, such as tetrahydrofuran or methylene chloride. An organic nitrogen base, such as triethylamine and the like, is then added to the reaction solution followed immediately by a silylating agent, such as triethylsilyl trifluoromethanesulfonate to provide intermediate C2. An aprotic polar coordinating solvent, such as DMF, 1-methyl-2-pyrrolidinone and the like, is added. This is followed by the addition of a palladium compound, such as tris(dibenzylideneacetone)dipalladium-chloroform, palladium acetate and the like, and the stannane C3. A metal halide, such as lithium chloride, zinc chloride, and the like tetrabutylammonium chloride and the like, is optionally added and the reaction solution is allowed to warm and is stirred at a suitable temperature, such as 0° to 50° C., for a few minutes to 48 hours. The carbapenem C4 is obtained by conventional isolation/purification methodology known in the art.

FLOW SHEET C

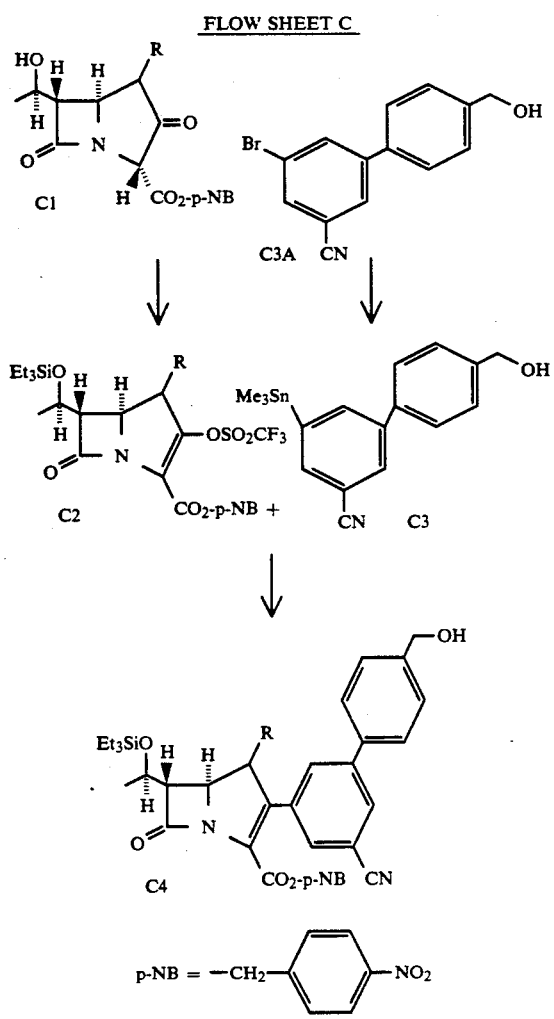

p-NB = —CH$_2$—⟨phenyl⟩—NO$_2$

Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257., L. D. Cama et al. *Tetrahedron*, 39, 2531 (1983); R. N. Guthikonda et al. *J. Med. Chem.*, 30, 871 (1987) hereby incorporated by reference.

The steps for preparing the 2-oxocarbapenam intermediate C1 are well known in the art and are explained in ample detail by D. G. Melillo et al., *Tetrahedron Letters*, 21, 2783 (1980), T. Salzmann et al., *J. Am. Chem. Soc.*, 102, 6161 (1980), and L. M. Fuentes, I. Shinkai, and T. N. Salzmann, *J. Am. Chem. Soc.*, 108, 4675 (1986). The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been been found that the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 23 (8), 1915 (1985); BE 900 718 A (Sandoz) and Japanese Patent Pub. No. 6-0163-882-A (Sanruku Ocean).

In preferred compounds of Formula I, $R^1$ is hydrogen. More preferably, $R^1$ is hydrogen and $R^2$ is (R)—CH$_3$CH(OH)— or (R)—CH$_3$CH(F)—. In the most preferred case, $R^1$ is hydrogen and $R^2$ is (R)—CH$_3$CH(OH)—. While R=H is usually preferred, there are instances in which R=CH$_3$ may provide improved chemical stability, water solubility, or pharmacokinetic behavior. The substituent R=CH$_3$ may be of either configuration, i.e., the α or β-stereoisomer.

Preferred $R^c$ are chosen from the group:

| | |
|---|---|
| —CF$_3$, | —CH$_2$CH$_2$NHCOCH$_3$ |
| —CH$_2$CH$_2$Cl, | —CH$_2$CH$_2$NHCOOCH$_3$ |
| —CH$_2$CH$_2$OCH$_2$CH$_3$ | —CH$_2$CH$_2$NHCONH$_2$ |
| —CH$_2$CH$_2$OCH$_2$CH$_2$OH | —CH$_2$CH$_2$NHSO$_2$CH$_3$ |
| —CH$_2$CH$_2$OCOCH$_3$ | —CH$_2$CH$_2$CHO |
| —CH$_2$CH$_2$OCO-phenyl | —CH$_2$CH$_2$COphenyl |
| —CH$_2$CH$_2$OCO-phenyl-p-OH | —CH$_2$CH$_2$(C=NOH)H |
| —CH$_2$CH$_2$OCONHCH$_3$ | —CH$_2$CH$_2$COOCH$_3$ |
| —CH$_2$CH$_2$SOCH$_3$ | —CH$_2$CH$_2$CON(OH)CH$_3$ |
| —CH$_2$CH$_2$SO$_2$CH$_3$ | —CH$_2$CH$_2$CSNH$_2$ |
| —CH$_2$CH$_2$SO$_2$NH$_2$ | —CH$_2$CH$_2$SCN |
| —CH$_2$CH$_2$N$_3$ | —CH$_2$CH$_2$SCF$_3$ |
| —CH$_2$CH$_2$NHCHO | —CH$_2$CH$_2$NH$_2$, and |
| —CH$_2$CH$_2$NCH$_3$CHO | —CH$_2$CH$_2$N(CH$_3$)$_2$ |

Most preferred $R^c$ substituents are:

| | |
|---|---|
| —CH$_3$, | —CH$_2$CH$_2$CH$_2$OCONH$_2$ |
| —CH$_2$CH$_2$OH, | —CH$_2$CH$_2$CONH$_2$, |
| —CH$_2$CH$_2$CH$_2$OH, | —CH$_2$CH$_2$OCONH$_2$, |
| —CH$_2$CONH$_2$, | —CH$_2$CN, |
| —CH$_2$CH$_2$CH$_2$CONH$_2$, and | —CH$_2$CH$_2$CN. |

The objective of the third synthetic stage is to substitute imidazole with the desired $R^c$. Applicants recommend three general alternative reactions towards this end. In one recommended reaction, the imidazole is N-alkylated according to Flow Sheet D1. In Flow Sheet D1, imidazole is N-alkylated at room temperature with cesium carbonate and the bromide or iodide of the desired $R^c$ in acetonitrile.

FLOW SHEET D1

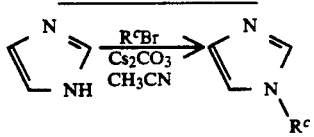

In another recommended reaction, the imidazole is N-alkylated according to Flow Sheet D2. In Flow Sheet D2, imidazole is N-alkylated at room temperature in DMF by first adding NaH to DMF and subsequently adding the bromide or iodide of the desired $R^c$.

FLOW SHEET D2

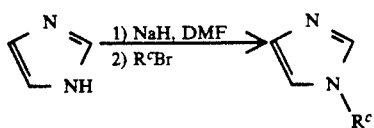

In another recommended reaction, the imidazole is N-alkylated according to Flow Sheet D3. In Flow Sheet D3, imidazole is N-alkylated by refluxing in acetonitrile with the bromide or iodide of the desired $R^c$.

FLOW SHEET D3

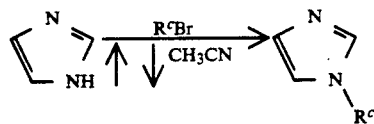

The objective of the fourth stage synthesis is to substitute the hydroxy portion of the hydroxymethyl substituent on the 2-biphenyl with $R^c$ substituted imidazolium. Two procedures are suggested herein. Depending upon the $R^c$ substituent, it may be preferable to choose one procedure over the other. Both procedures follow the basic scheme depicted in Flow Sheet E. Referring to Flow Sheet E, the hydroxy moiety is replaced with leaving group Z. Subsequently, the imidazole displaces Z to form a protected compound of Formula I. Details of the two procedures follow Flow Sheet E.

FLOW SHEET E

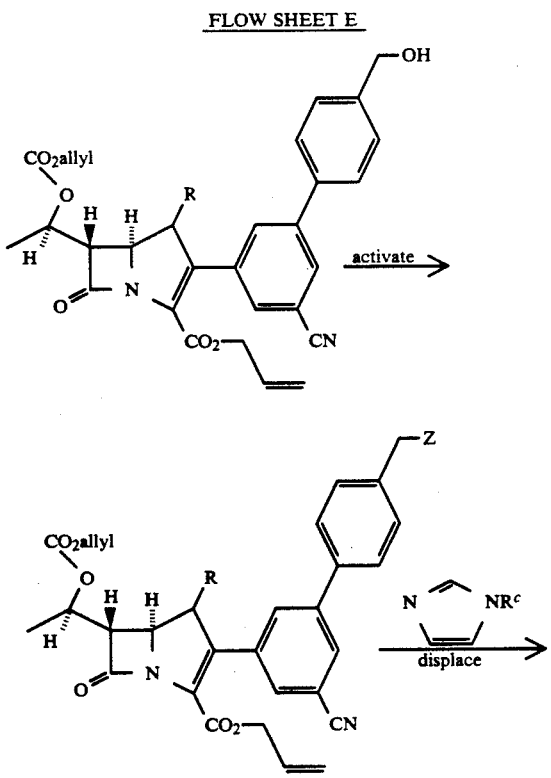

-continued
FLOW SHEET E

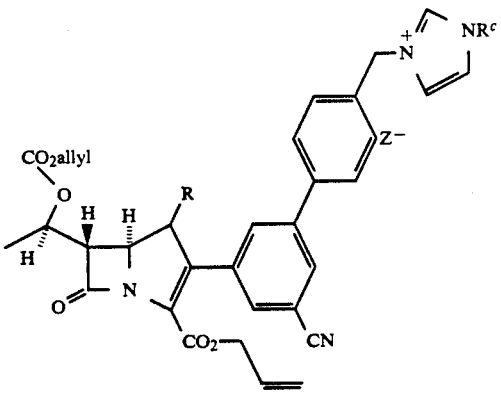

For a first procedure, the hydroxyl group of —CH$_2$OH on 2-biphenyl may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate may converted to the reactive iodide derivative by treatment with sodium iodide in a suitable solvent, e.g., acetone, at reduced or ambient temperatures. Alternatively, &he hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the imidazolium substituent is accomplished simply by treating the iodide with the desired compound, e.g. N-methylimidazole. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desireable.

For a second procedure, the hydroxyl group of —CH$_2$—OH on 2-biphenyl may be converted into the reactive trifluoromethanesulfonate (triflate) group. However, such an activating group may not be isolated by conventional techniques but can be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butylpyridine in a suitable solvent, such as dichloromethane, at reduced temperatures provides for the generation of the triflate activating group. Introduction of the imidazolium group is then accomplished by reacting the above triflate in situ with the desired imidazole compound at reduced temperature. In certain cases it is possible and desireable to use the reacting imidazole as the base for the formation of the triflate activating group. In this case treatment of the hydroxyl group with triflic anhydride in the presence of at least two equivalents of the reacting imidazole under the conditions described above provides the cationic substituent.

The following are representative of suitable and alternative leaving groups; alkyl and substituted alkylsulfonates, aryl and substituted arylsulfonates, and halide. The common sulfonate leaving groups are: methanesulfonyloxy, trifluoromethanesulfonyloxy, fluorosulfonyloxy, p-toluenesulfonyloxy, 2,4,6-tri-isopropylbenzenesulfonyloxy, p-bromo-benzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride.

In the preparation methods described above, the carboxyl group at the 3-position and the hydroxyl group at the 8-position of the carbapenem remain blocked by protecting groups until the penultimate product is prepared. Suitable hydroxyl protecting groups, P', are triorganosilyl groups such as trialkylsilyl, aryl(dialkyl)silyl, and diarylalkylsilyl and carbonate groups such as alkyloxycarbonyl and substituted alkyloxycarbonyl, benzyloxycarbonyl and substituted benzyloxycarbonyl and allyloxycarbonyl and substituted allyloxycarbonyl. The preferred protecting groups are methoxy-t-bu tylphenylsilyl, t-butyldiphenylsilyl, trimethylsilyl, triethylsilyl, o-nitrobenzyloxycarbonyl, p-nitrobenzyloxycarbonyl, benzyloxycarbonyl, t butyloxycarbonyl, 2,2,2-trichloroethyloxycarbonyl and allyloxycarbonyl. Suitable carboxyl protecting groups, M, in addition to or including those shown in the schemes are described hereinbelow.

Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like in an organic solvent such as tetrahydrofuran at 0° C. to ambient temperature for from a few minutes to several hours. The resulting desilylated carbapenem may be isolated by conventional techniques, but is more conveniently taken into the final deprotection process. Thus, addition of an inorganic base such as $NaHCO_3$ or $KHCO_3$ and 10% Pd/C followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be $COO^-$. However, where M is, e.g., a pharmaceutically acceptable ester, a counterion (anion) $Z^-$ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by COOM= $COO^-$. In that case, it will be understood that it is necessary to provide a counterion (cation) for the anionic substituent. However, it is well within the skill of a medicinal chemist, to whom there is available many suitable anionic and cationic counterions, to make such choices.

Listed in Table I are specific compounds of the instant invention:

TABLE I

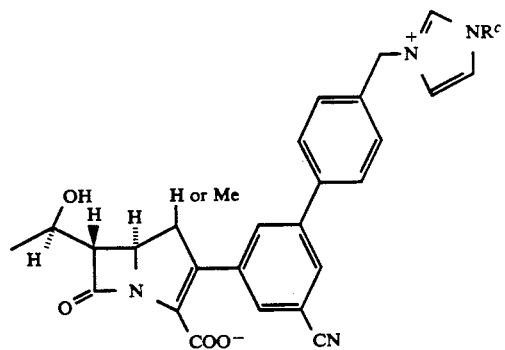

where $R^c$ is selected from the group consisting of:

| | |
|---|---|
| $-CH_3$, | $-CH_2CH_2CH_2OCONH_2$ |
| $-CH_2CH_2OH$, | $-CH_2CH_2CONH_2$, |
| $-CH_2CH_2CH_2OH$, | $-CH_2CH_2OCONH_2$, |
| $-CH_2CONH_2$, | $-CH_2CN$, |
| $-CH_2CH_2CH_2CONH_2$, and | $-CH_2CH_2CN$. |

The carbapenem compounds of the present invention are useful per se and in their pharmaceutically acceptable salt and ester forms in the treatment of bacterial infections in animal and human subjects. The term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Examples of such ester protecting groups include benzhydryl, p-nitrobenzyl, 2-naphthylmethyl, allyl, benzyl, trichloroethyl, silyl such as trimethyl silyl or t-butyldiphenylsilyl phenacyl, p-methoxybenzyl, acetonyl, o-nitrobenzyl, 4-pyridylmethyl, and $C_1-C_6$ alkyl such as methyl, ethyl or t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include; topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the antibacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occurring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (U.S. Pat. No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.define the procedure for determining DHP susceptibility of the present carbapenems and 2.disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

EXAMPLE 1

Preparation of 4-Amino-3,5-dibromobenzonitrile

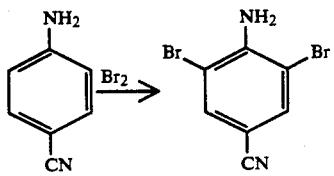

To a stirred solution of 100 mg (0.847 mmoles) of p-aminobenzonitrile in 3.6 mL dioxane chilled in an ice-bath was added sequentially 356 µL (1.78 mmoles) of 5 N sodium hydroxide solution and 284 mg (1.78 mmoles) of bromine. The ice-water bath was removed and the reaction mixture was stirred further for 1.5 hours. After this time, 21.8 µL (0.423 mmoles) of bromine was added to drive the reaction to completion and stirring was continued for 10 minutes.

The mixture was partitioned between ethyl acetate and ice-water and the organic phase was separated. It was washed with brine, dried over anhydrous sodium sulfate, filtered, and evaporated.

Purification by plate layer chromatography using hexane-ethyl acetate (7:3) as eluant provided 175 mg (74%) of the entitled product.

NMR(CDCl$_3$) δ: 5.1 (bs, 2H), 7.66 (s, 2H).

EXAMPLE 2

Preparation of 3,5-Dibromobenzonitrile

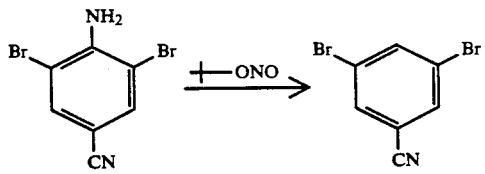

To a stirred solution of t-butylnitrite (53.5 µL, 0.449 mmoles) in 1 ml sieve dried dimethylformamide at 50° C. under an atmosphere of nitrogen was added a solution of 4-amino-3,5-dibromobenzonitrile (50 mg, 0.179 mmoles) in 1 mL of DMF. The mixture was stirred at 50° C. for 0.5 hour and partitioned between diethyl ether, ice-water, and ammonium chloride. The organic phase was separated, washed with water and brine, dried over anhydrous sodium, filtered, and evaporated.

Purification by plate layer chromatography using hexane-ethyl acetate (9:1) as eluant provided 28 mg (59%) of white, crystalline product.

NMR(CDCl$_3$) δ: 7.7 (d, J=1.8Hz, 2H), 7.9 (t, J=1.8Hz, 1H).

EXAMPLE 3

Preparation of 4-t-butyldiphenylsiloxymethylbromobenzene

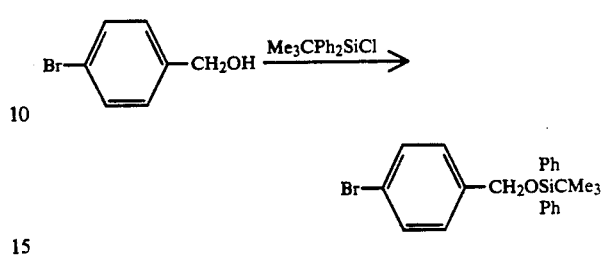

To a stirred solution of 7.48 g (40 mmoles) of p-bromobenzyl alcohol and 6.07 g (60 mmoles) of triethylamine in 70 mL of sieve dried DMF at 0° C. was added 14.3 g (52 mmoles) of neat t-butyldiphenylsilylchloride. The ice-water bath was removed and the mixture was stirred further for 20 hours.

The mixture was partitioned between ether, ice-water, and 2 N hydrochloric acid, and the organic phase was separated, washed with water and brine, dried over anhydrous sodium sulfate, filtered, and evaporated.

Purification by column chromatography on 200 g of EM-60 silica gel eluting with hexanes-methylene chloride (3:1) gave 15.9 g (94%) of the title compound.

NMR(CDCl$_3$) δ: 1.1 (s, 9H), 4.72 (s, 2H), 7.22 (d, J=8.3 Hz, 2H), 7.43 (m, 8H), 7.7 (m, 4H).

EXAMPLE 4

Preparation of 4-t-butyldiphenylsiloxymethylphenylboronic acid

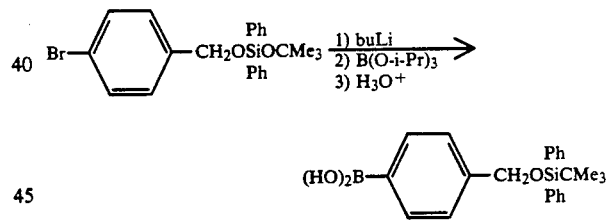

To a stirred solution of p-t-butyldiphenylsiloxymethylbromobenzene (10.1 g, 23.8 mmoles) in 100 mL of dry tetrahydrofuran at −78° C. under nitrogen was added dropwise 9.9 mL (25.0 mmoles) of 2.5 M n-butyllithium in hexane. The mixture was stirred at −78° C. for 15 minutes and 4.7 g (25.0 mmoles) of triisopropylborate was added. After 5 minutes, the low temperature bath was removed, and the mixture was stirred further for 1.5 hours.

The mixture was poured onto ice-2N hydrochloric acid and ether was added. The biphasic mixture was stirred for 0.5 hour and the organic phase was separated, washed with brine, dried over anhydrous sodium sulfate, filtered, and evaporated to give 8.8 g (94.2%) of crude product.

Precipitation from an ether-methylene chloride solution of the crude material with hexanes gave 7.1 g (76%) from two crops.

NMR(CDCl$_3$)δ: (s, 9H), 4.89 (s, 2H), 7.44 (m, 6H), 7.52 (d, J=7.8Hz, 2H), 7.74 (m, 4H), and 8.25 (d, J=7.8Hz, 2H).

EXAMPLE 5

Preparation of 3-bromo-5-cyano-4'-t-butyldiphenylsilyloxymethyl-biphenyl

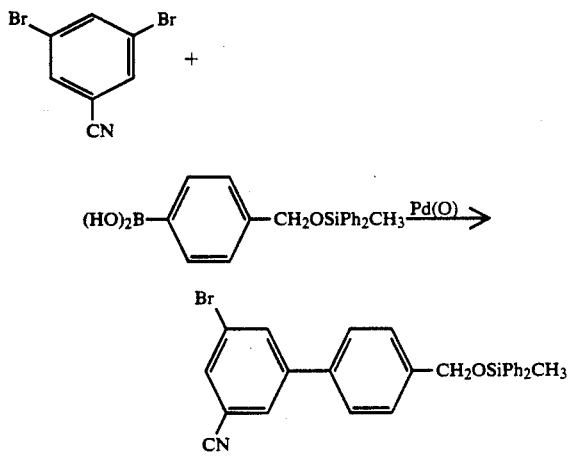

A mixture of 1.49 g (3.83 mmoles) of boronic acid derivative from Example 4, 2.0 g (7.67 mmoles) of 3,5-dibromobenzonitrile, and 133 mg (0.1 mmoles) of tetrakistriphenylphosphine in 16 mL toluene and 3.4 mL 95% ethanol with 3.47 mL (6.97 mmoles) of 2 N sodium carbonate was stirred vigorously at 80° C. under nitrogen for 3.5 hours.

The mixture was partitioned between ethyl acetate and ice-water and the organic phase was separated, washed with water and brine, dried over anhydrous sodium sulfate, filtered, and evaporated to give 2.4 g of residue.

The product can be purified by silica gel chromatography but was more conveniently purified after desilylation as described in Example 6.

NMR(CDCl$_3$) δ: 1.12 (s, 9H), 4.83 (s, 2H), 7.41–7.54 (m, 10H), 7.69–7.76 (m, 5H), 7.8 (t, J =1.6Hz, 1H), 7.96 (t, J=1.6Hz, 1H).

EXAMPLE 6

Preparation of 3-Bromo-5-cyano-4'-hydroxymethyl biphenyl

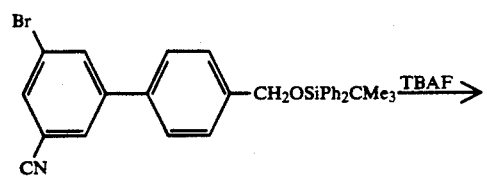

The residue 2.4 g from Example 5 was dissolved in 25 mL of dry THF and stirred while 784 μL (13.7 mmoles) of acetic acid and 4.79 mL (4.79 mmoles) of a 1 M solution of tetrabutylammonium fluoride in THF were added. The resulting mixture was stirred at ambient temperature for 18 hours and then partitioned between ethyl acetate and ice-water. The organic phase was separated, washed with dilute sodium bicarbonate solution and brine, dried over anhydrous sodium sulfate, filtered, and evaporated.

Purification by silica gel chromatography using methylene chloride-ethyl acetate (10:1) as eluant gave 908 mg (82% overall) of the title compound.

NMR(CDCl$_3$) δ: 1.73 (t, J=5.8Hz, 1H), 4.78 (d, J=5.8Hz, 2H), 7.47–7.57 (m, 4H), 7.75 (m, 1H), 7.79 (m, 1H), 7.95 (m, 1H).

EXAMPLE 7

Preparation of 3-trimethylstannyl-5-cyano-4'-hydroxymethylbiphenyl

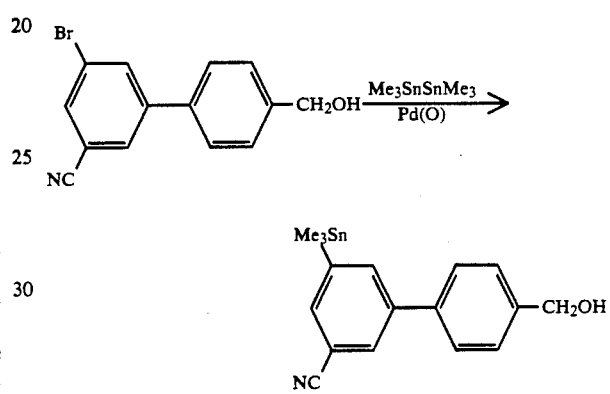

A stirred mixture of 1.76 g (6.1 mmoles) of 3-bromo-5-cyano-4'-hydroxymethylbiphenyl, 353 mg, (0.31 mmoles) of tetrakistriphenylphosphine, 48 mg (0.18 mmoles) of triphenylphosphine and 2.4 mL (12.2 mmoles) of hexamethylditin in 17.1 mL of toluene was heated at 110° C. for 1.5 hours.

The cooled mixture was partitioned between EtOAc and ice-water and the organic phase separated, washed with water and brine, dried over anhydrous sodium sulfate, filtered, and evaporated.

Purification by silica gel chromatography with methylene chloride-ethyl acetate (10:1) as eluant gave 2.21 g (93%) of the title compound, as an oil.

NMR(CDCl$_3$) δ: 0.37 (s, 9H), 1.72 (t, J=5.9Hz), 4.76 (d, J=5.9Hz, 2H), 7.46–7.58 (m, 4H), 7.72 (m, 1H), 7.76 (m, 1H), 7.86 (m, 1H).

EXAMPLE 8

Preparation of Carbapenem 1

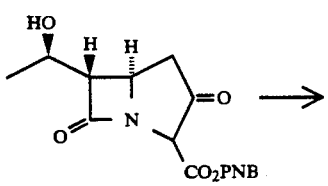

-continued

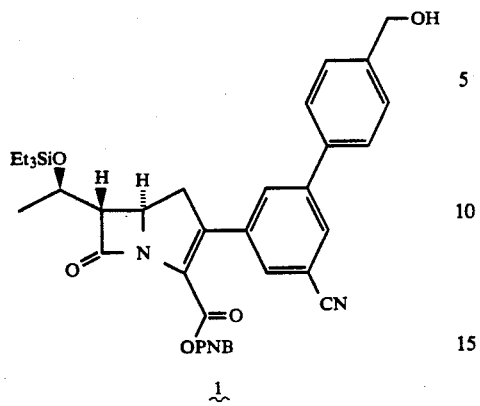

1

To a stirred solution of 2.04 g (5.86 mmoles) of keto ester in 42 mL of dry methylene chloride at 0° C. under nitrogen was added 902 µL (5.18 mmoles) of diisopropylethyl amine. The mixture was cooled to −78° C. and 795 µL (4.73 mmoles) of triflic anhydride was added. After stirring for 20 minutes 942 µL of diisopropylethylamine was added and stirring continued for 15 minutes. Triethylsilyltriflate (1.12 mL, 4.96 mmoles) was then added and the mixture stirred 20 minutes longer. After this time, a solution of 3-trimethylstannyl-5-cyano-4'-hydroxymethylbiphenyl (1.68 g, 4.5 mmoles) in 17 mL of N-methylpyrrolidinone was added along with 50.6 mg (0.23 mmoles) of palladium acetate. The low temperature bath was removed and the stirred solution was bought to room temperature with a warm water bath. The mixture was stirred at ambient temperature for 1 hour and 50.6 mg of additional palladium acetate was added. After stirring 2 hours longer the mixture was partitioned between EtOAc and ice-water. The organic phase was separated, washed with water and brine, dried over anhydrous sodium sulfate, filtered and evaporated.

Purification by silica gel chromatography provided 1.46 g (50%) of biphenylcarbapenem 1.

NMR(CDCl3) δ: 0.62 (q, J=7Hz, 6H), 0.97 (t, J=7Hz, 9H), 1.3 (d, J=6.1Hz, 3H), 3.24–3.35 (m, 3H), 4.26–4.37 (m, 2H), 4.77 (s, 2H), 5.19 (d, J=13.4Hz, 1H), 5.38 (d, J=13.4Hz, 1H), 7.47–7.58 (m, 7H), 7.77 (m, 2H), 8.1 (d, J=8.8Hz, 2H).

EXAMPLE 9

Preparation of Carbapenem 2

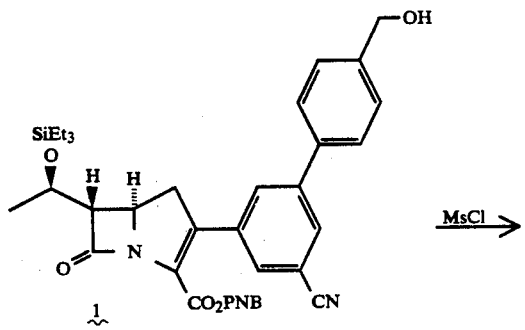

-continued

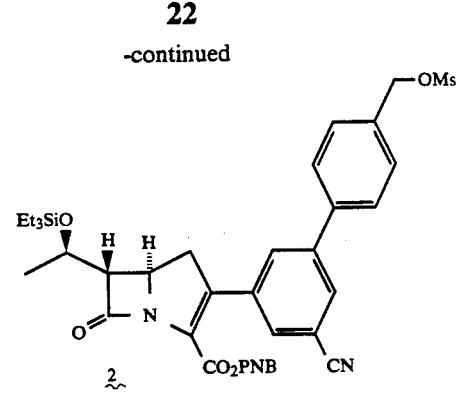

2

To a stirred solution of 1.0 g (1.53 mmoles) of 1 and 406 µL (2.91 mmoles) of triethylamine in 15 mL sieve dried methylene chloride at 0° C. under nitrogen was added 189.6 µL (2.45 mmoles) of mesyl chloride. The mixture was stirred at 0° C. for 15 minutes and the mixture was partitoned between EtOAc, ice-water, and 2 N hydrochloric acid. The organic phase was separated, washed with brine, dried over anhydrous sodium sulfate, filtered and evaporated to give 1.16 g (100%) of crude product 2 which was used immediately without further purification.

NMR(CDCl3) δ: 0.62 (q, J=7.5Hz, 6H), 0.97 (t, J=7.5Hz, 9H), 1.30 (d, J=6.4Hz, 3H), 3.01 (s, 3H), 3.25–3.35 (m, 3H), 4.26–4.37 (m, 2H), 5.21 (d, J=13.3Hz, 1H), 5.3 (s, 2H), 5.39 (d, J=13.3Hz, 1H).

EXAMPLE 10

Preparation of Carbapenem 3

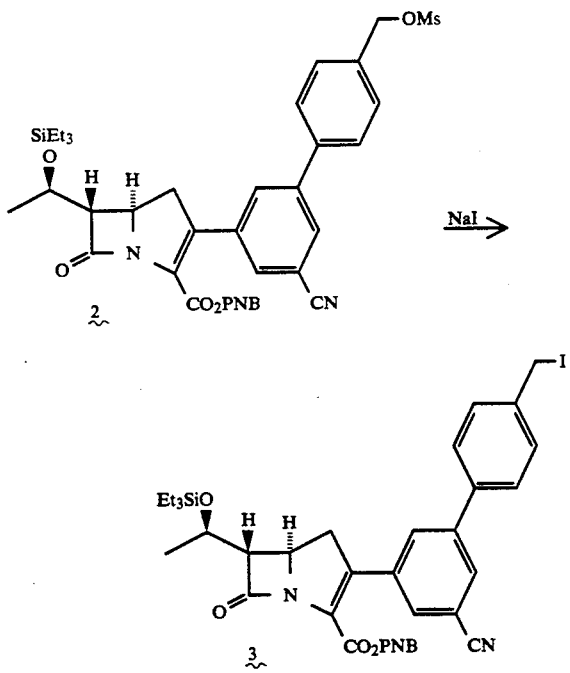

The crude mesylate 2 from Example 9 in 15 mL acetate was stirred with 456 mg (3.06 mmoles) of sodium iodide at ambient temperature for 45 minutes. The mixture was partitioned between ethyl acetate, ice-water, and 5% aqueous sodium thiosulfate and the organic phase separated, washed with brine, dried over anhydrous sodium sulfate, filtered, and evaporated to give 1.16 g (97%) of crude iodide 3 which was of sufficient purity to use as is.

NMR(CDCl₃) δ: 0.64 (q, 6H), 0.96 (t, 9H), 1.3 (d, J=6.2Hz, 3H), 3.24–3.33 (m, 3H), 4.25–4.35 (m, 2H), 4.5 (s, 2H), 5.2 (d, J=13.3Hz, 1H), 5.38 (d, J=13.3Hz, 1H), 7.4–7.6 (m, 7H), 7.77 (m, 2H), 8.15 (d, J=8.8Hz, 2H).

EXAMPLE 11

Preparation of N-t-butyldimethylsilyloxyethyl imidazole

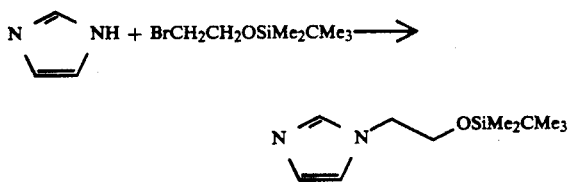

To 86.4 mg (2.2 mmoles) of 61.1% sodium hydride mineral oil dispersion in 5 mL sieve dried DMF at 0° C. was added 136 mg (2.0 mmoles) of imidazole. The mixture was stirred at 0° C. under nitrogen for 15 minutes and 476 mg (2.0 mmoles) of neat t-butyldimethylsilyloxyethyl bromide was added. The ice-water bath was removed and the mixture stirred overnight and it was then partitioned between ether and ice-water. The organic phase was separated, washed thrice with ice-water, dried over sodium sulfate, filtered, and evaporated to give 282.3 mg (63%) of the title compound.

NMR(CDCl₃) δ: −0.05 (s, 6H), 0.85 (s, 9H), 3.82 (t, J=5.2Hz, 2H), 4.02 (t, J=5.2 Hz, 2H), 6.92 (bs, 1H), 7.02 (bs, 1H), 7.48 (bs, 1H).

EXAMPLE 12

Preparation of Carbapenem 4

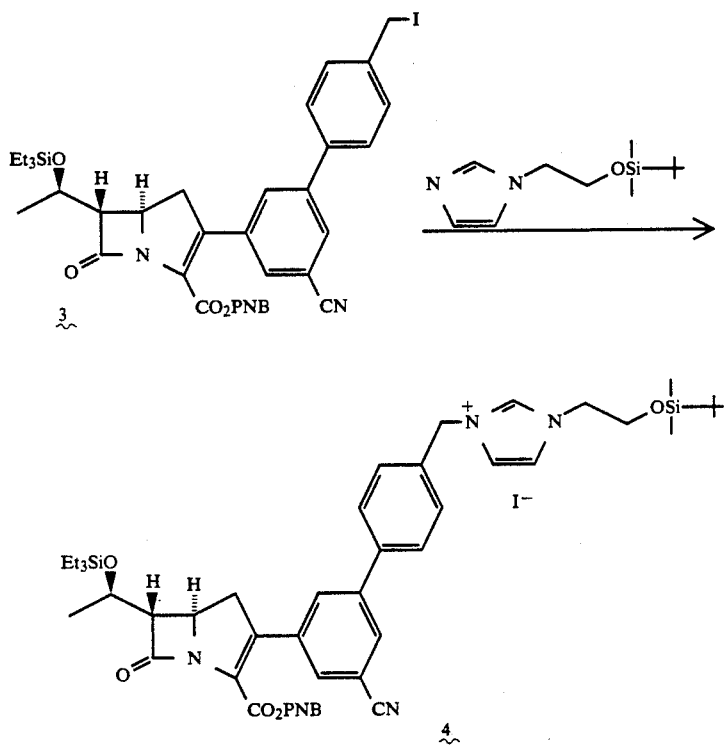

The iodide 3 from Example 10 with 693 mg (3.06 mmoles) of N-t-butyldimethylsilyloxyethyl imidazole in 15 mL sieve dried acetonitrile was stirred at ambient temperature for 15.5 hours. The mixture was partitioned between methylene chloride and ice-water and the aqueous phase was separated, washed with ice-H₂O dried over anhydrous sodium sulfate, filtered, and evaporated. The residue was dissolved in a minimum amount of methylene chloride and the product was precipitated by the addition of ether. Repetition of the process give 1.33 g (88%) of carbapenem 4.

NMR(CDCl₃) δ: 0.02 (s, 6H), 0.62 (q, 6H), 0.83 (s, 9H), 0.97 (t, 9H), 1.3 (d, J=6Hz, 3H), 3.25–3.46 (m, 3H), 4.02 (t, J=4.0Hz, 2H), 4.27–4.48 (m, 2H), 4.52 (t, J=4Hz, 2H), 5.21 (d, J=13.3Hz, 1H), 5.4 (d, J=13.3Hz, 1H), 5.62 (s,2H), 7.4–8.15 (m, 11H).

EXAMPLE 13

Preparation of Carbapenem 5

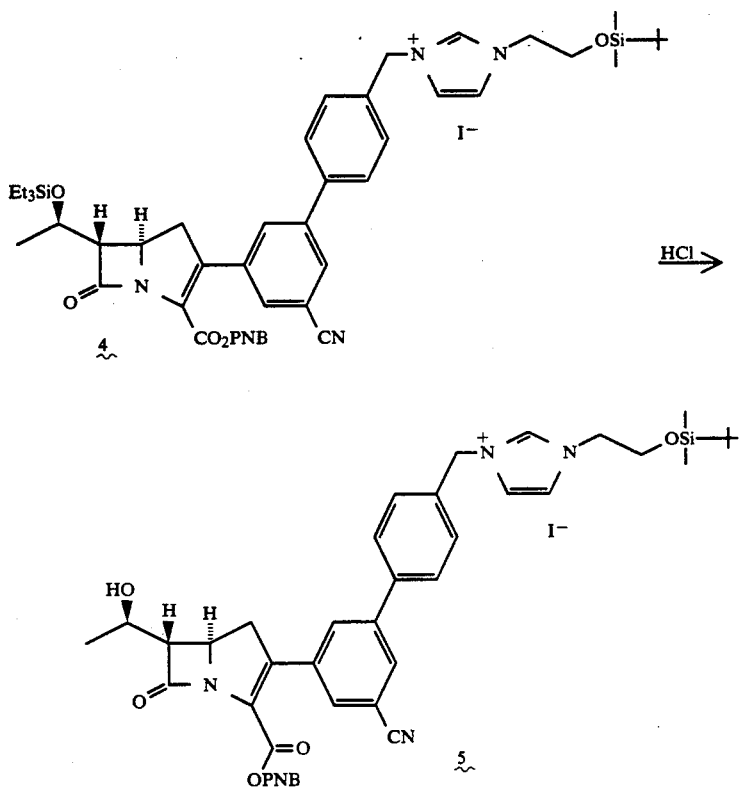

To a stirred solution of carbapenem 4 (1.33 g, 1.52 mmoles) from Example 12 in 60 mL of THF-$H_2O$ (1:1) at 0° C. under nitrogen was added 378 μL (0.76 mmoles) of 2 N hydrochloric acid. The ice-water bath was removed and the reaction mixture was stirred further for one hour. To the mixture was added 1.08 mL (0.76 mmoles) of 0.7 M sodium bicarbonate solution and the volatiles were removed under reduced pressure. The residue was extracted with methylene chloride and the extract was washed with water, dried over anhydrous sodium sulfate, filtered, and evaporated. The residue was taken up in a minimum amount of methylene chloride and the product 5 was precipitated by the addition of ether. Repetition of this process and drying in vacuo gave 1.1 g (96%) of 5 as a yellow foam.

NMR(CDCl$_3$) δ: 0.13 (s, 6H), 0.83 (s, 9H), 1.40 (d, J=6.2Hz, 3H), 3.3–3.48 (m, 3H), 4.0 (t, J=4.5Hz, 2H), 4.31 (m, 1H), 4.4–4.53 (m, 3H), 5.17 (d, J=13.4Hz, 1H), 5.37 (d, J =13.4Hz, 1H), 5.62 (s, 2H), 7.37–7.77 (m, 11H), 8.07 (d, J=8.8Hz, 2H).

EXAMPLE 14

Preparation of Carbapenem 6

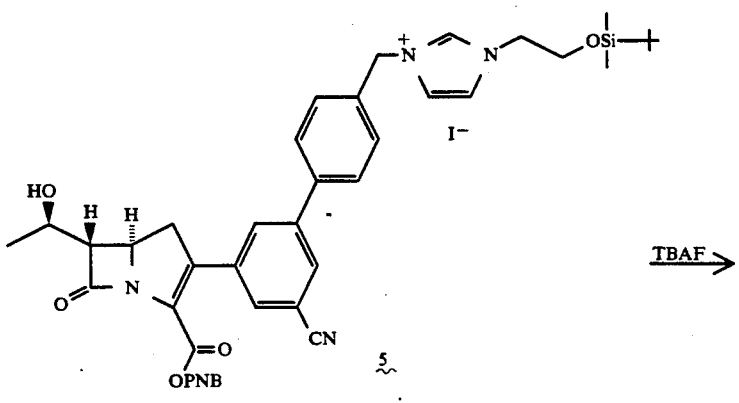

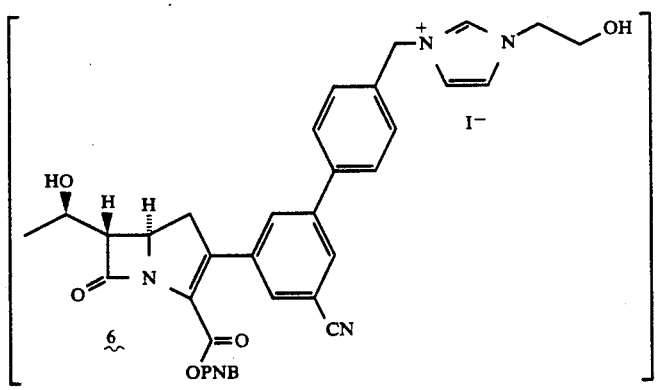

To a stirred solution of 33.0 mg (0.038 mmoles) of 5 in 3 mL THF at 0° C. under nitrogen was added sequentially 6.5 μL (0.113 mmoles) of acetic acid and then 39.6 μL (0.039 mmoles) of a 1 M solution of tetrabutylammonium fluoride in THF. The reaction mixture was stirred at 0° C. for 3 hours, after which time another 39.6 μL of TBAF solution was storage in the cold overnight. 162 μL (0 113 mmoles) of 0.7 M sodium bicarbonate solution was added. The solution containing 6 was used as described in Example 15.

EXAMPLE 15

Preparation of Carbapenem 7 trile (3:1) as eluant gave, after extraction of the product band with acetonitrile-water (4:1), concentration, and lyophilization, 7.0 mg (49%) of 7.

IR (NuJol); 2225, 1760, 1590 cm$^{-1}$.

400 MHz NMR($D_2O$—$CD_3CN$,3:1) δ: 1.5 (d, J=6.4Hz, 3H), 3.31 (dd, J=9.9, 16.8Hz, 1H), 3.65 (dd, J=8.5, 16.8Hz, 1H), 3.68 (dd, J=2.8, 6.1Hz, 1H), 4.1 (t, J=4.9Hz, 2H), 4.4 (p, 6.2Hz, 1H), 4.5 (m, 3H), 5.66 (s, 2H), 7.73-8.18 (m, 9H), 9.09 (bs, 1H). HDO-4.82

UV($H_2O$): λ$_{max}$ 305, 258 nm.

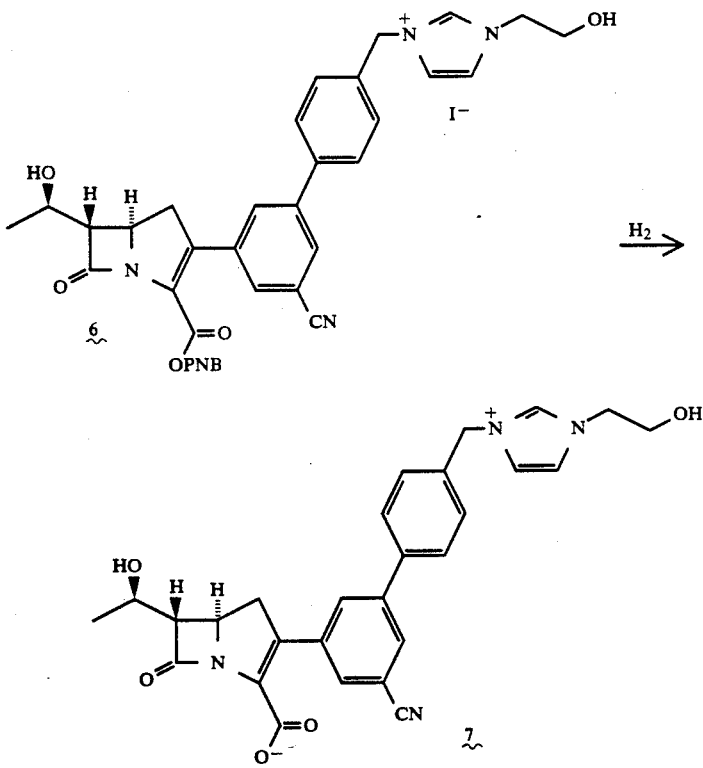

To the mixture of Example 14 was added 1 mL water, 0.3 mL of 0.2 M pH 7 phosphate buffer, and 5.0 mg of 5% Rh on alumina and the stirred mixture was hydrogenated at 0° C. for 4 hours. After this time the catalyst was removed by filtration through celite. Concentration under reduced pressure and purification by reverse phase plate layer chromatography using water-acetoni-

EXAMPLE 16

Preparation of 3,5-dibromo-4'-t-butyldiphenylsilyloxymethylbiphenyl

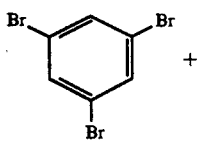
+
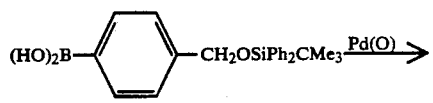
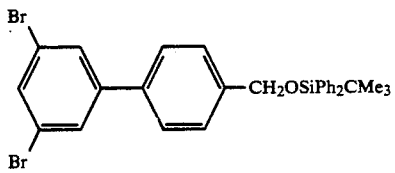

Utilizing the Suzuki reaction outlined in Example 5, 15.0 g (38.5 mmoles) of boronic acid derivative with 36.5 g (115.4 mmoles) of 1,3,5-tribromobenzene and 1.33 g (1.15 mmoles) of tetrakistriphenylphosphine in 140 mL of toluene and 35 mL ethanol and 35 mL 2 N solution carbonate solution gave, after 4 hours at 80° C. and chromatography, 17.8 g (80%) of the title compound.

NMR(CDCl$_3$) δ: 1.11 (s, 9H), 4.82 (s, 2H), 7.35–7.73 (m).

EXAMPLE 17

Preparation of 3-Bromo-5-formyl-4'-t-butyldiphenylsilyloxymethyl-biphenyl

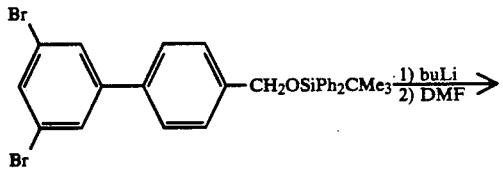

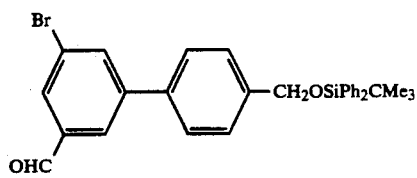

To a stirred solution of 100 mg (0.17 mmoles) of dibromide in 1 mL of dry THF at −78° C. under nitrogen was added 72 μL (0.18 mmole) of 1.05 M n-butyl lithium in hexanes. The mixture was stirred 5 minutes at −78° C. and then was added 26.6 μL (0.34 mmoles) of sieve dried DMF. The mixture was stirred further one hour and partitioned between ethyl acetate and ice-water. The organic phase was separated, washed in brine, dried over anhydrous sodium sulfate, filtered, and evaporated.

The residue was purified by plate layer chromatography eluting with hexane-ethyl acetate (4:1) to give 83 mg (91%) of the title compound.

NMR(CDCl$_3$) δ: 1.14 (s, 9H), 4.85 (s, 2H), 7.38–7.76 (m, 14H), 7.98–8.04 (m, 3H), 9.02 (s, 1H).

EXAMPLE 18

Preparation of 3-Bromo-5-dioxolanyl-4'-t-butyldiphenylsiloxymethyl biphenyl

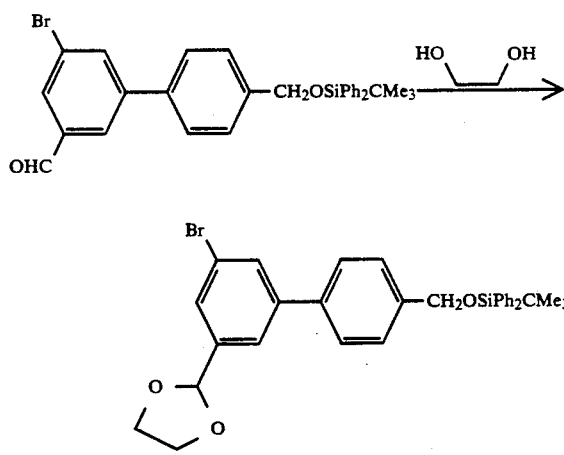

A stirred mixture of 5.3 g (10 mmoles) of aldehyde, 1.11 mL (20.0 mmoles) of ethylene glycol, and 190.6 mg (1 mmole) of p-toluene sulfonic acid monohydrate in 125 mL of benzene was refluxed with water removal via a Dean-Stark trap for 1 hour. The cooled mixture was partitioned between ethyl acetate and ice-water and the organic phase was separated. It was washed with saturated sodium bicarbonate solution and brine, dried over anhydrous sodium sulfate, filtered, and evaporated.

Purification by silica gel chromatography using hexane-methylene chloride (7:3) gave 5.1 g (89%) of title compound.

NMR(CDCl$_3$) δ: 1.12 (s, 9H), 4.05–4.15 (m, 4H), 4.82 (s, 2H), 5.86 (s, 1H), 7.36–7.74 (m, 17H).

EXAMPLE 19

Preparation of Azetidinone 8

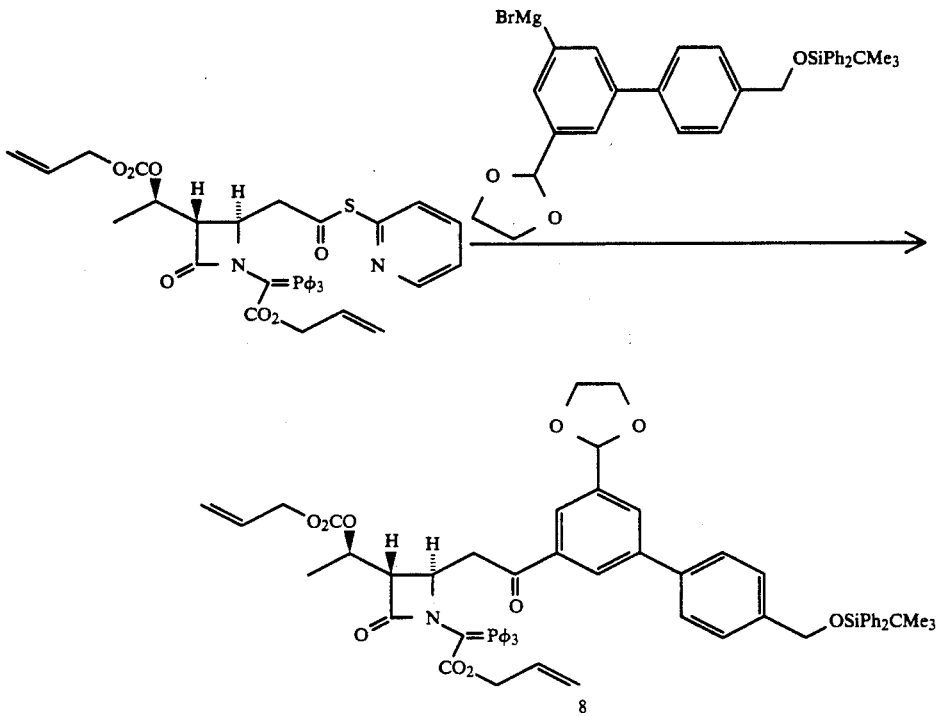

To a stirred mixture of 821.8 mg (33.82 mmoles) of magnesium turnings and 6.14 g (10.72 mmoles) of bromobiphenyl derivative from Example 18 in 38.7 mL of dry THF was added 387.6 μL of dibromoethane and the mixture was heated briefly with a heat gun to initiate the Grignard reaction. The hot mixture was stirred further for 6.5 hours during which time the administration of dibromoethane and heat was continued to drive the reaction to completion.

The solution of Grignard reagent was then added to a stirred solution of 7.98 g (11.27 mmoles) of pyridylthioester azetidinone derivative in 80 mL of dry THF at 0° C. The resulting mixture was stirred at 0° C. for one hour and then partitioned between ethyl acetate and ice-water. The organic phase was separated and washed with ice cold 5 N sodium hydroxide and brine, dried over sodium sulfate, filtered, and evaporated.

Purification by chromatography on silica gel eluting with hexane-ethyl acetate (3:2) provided 4.93 g (42%) of title compound.

IR (CH$_2$Cl$_2$) 1745, 1675, 1610 cm$^{-1}$.

EXAMPLE 20

Preparation of Azetidinone 9

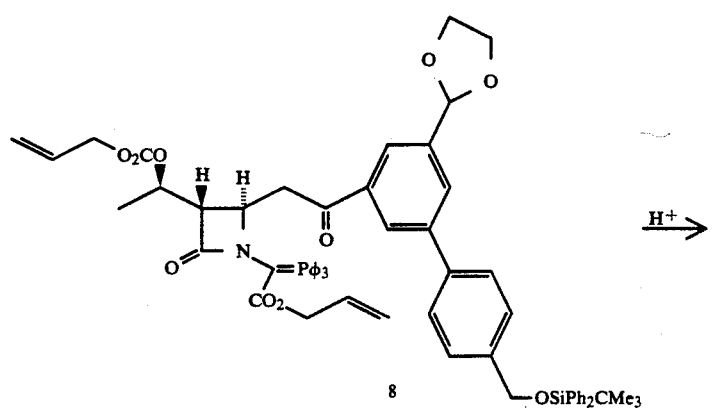

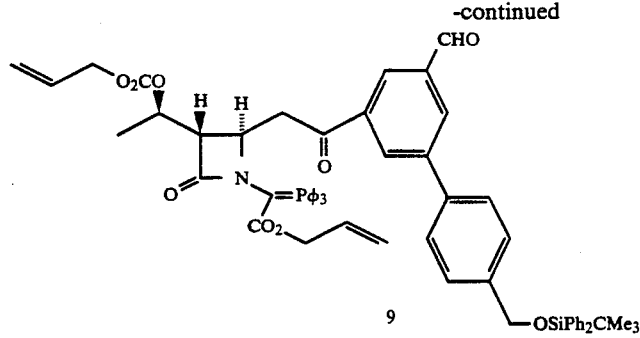

A solution of azetidinone 8 (50 mg, 0.046 mmoles) and 91.6 μL (0.18 mmoles) of 2 N hydrochloric acid and in 1 mL of THF was stirred at 0° C. under nitrogen for 28 hours. The mixture was partitioned between ethyl acetate, ice-water, and aqueous sodium bicarbonate solution, and the organic phase separated, washed with brine, dried over sodium sulfate, filtered, and evaporated.

Purification by plate layer chromatography using ethyl acetate-hexane (7:3) as eluant gave 36 mg (75%) of 9.

IR (CH$_2$Cl$_2$) 1745, 1705, 1680, 1610 cm$^{-1}$.

EXAMPLE 21

Preparation of Azetidinone 10

A mixture of 1.58 g (1.51 mmoles) of 9 and 105 mg (1.51 mmoles) of hydroxylamine hydrochloride in 24.5 mL of ethanol and 24.5 mL of pyridine was stirred at 0° C. for 5 minutes. The mixture was partitioned between ethyl acetate, ice-water and aqueous saturated ammonium chloride solution. The organic phase was separated, washed with aqueous sodium bicarbonate solution and brine, dried over sodium sulfate, filtered, and evaporated. The crude oxime derivative 10 was used without further purification.

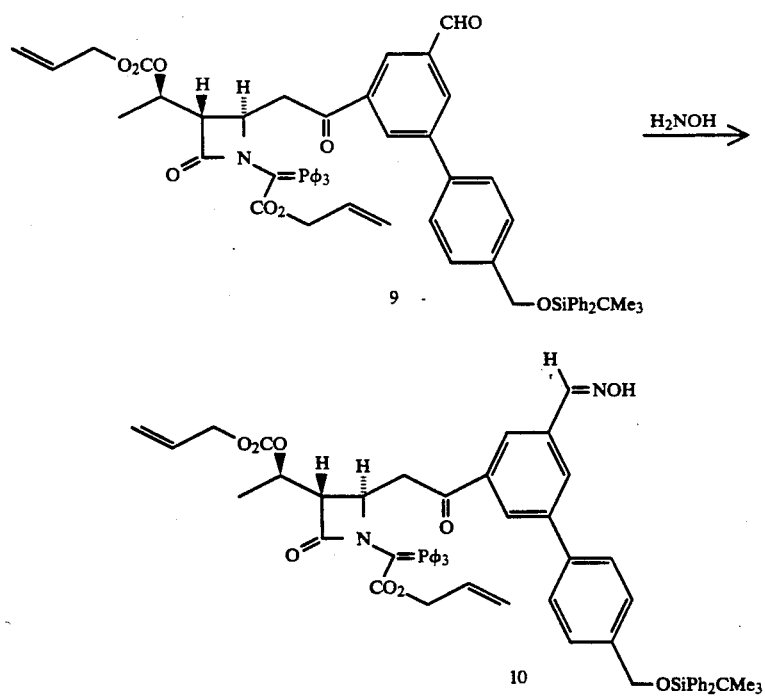

EXAMPLE 22

Preparation of Azetidinone 11

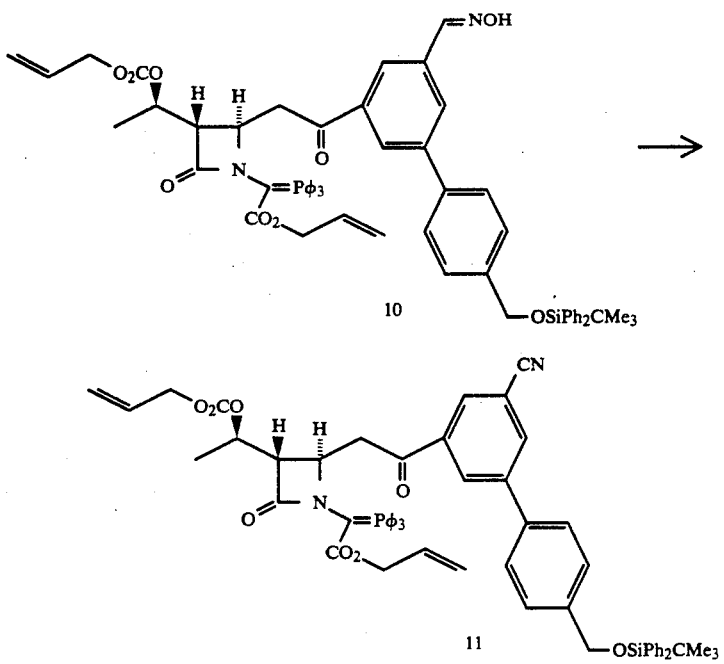

To a stirred solution of 1.61 g (1.51 mmoles) of oxime derivative 10 from Example 21 in 56 mL of sieve dried methylene chloride at −78° C. was added sequentially 463 μL (3.32 mmoles) of triethylamine and then 254 μL (1.51 mmoles) of triflic anhydride. The mixture was stirred at −78° C. for 15 minutes and was partitioned between ethyl acetate, ice-water, and aqueous ammonium chloride solution. The organic phase was separated, washed with aqueous sodium bicarbonate and brine, dried over sodium sulfate, filtered, and evaporated. Purification by chromatography on silica gel using hexane-ethyl acetate (6:4) as eluant gave 959 mg (61%) of 11.

IR (CH$_2$Cl$_2$) 2300, 1745, 1695, 1610 cm$^{-1}$.

EXAMPLE 23

Preparation of Azetidinone 12

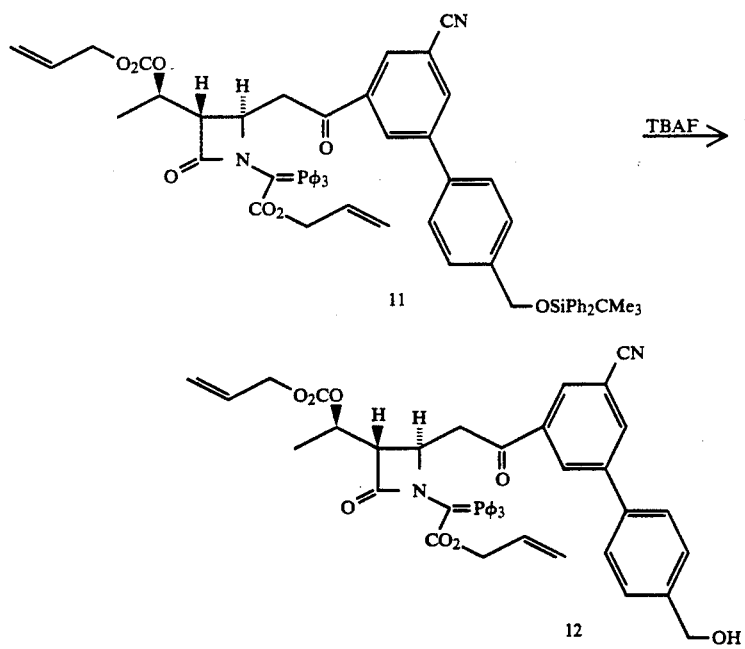

To a stirred solution of 2.68 g (2.57 mmoles) of 11 in 26.8 mL of dry THF at ambient temperature was added sequentially 441 μL (7.7 mmoles) of glacial acetic acid and then 2.82 mL (2.82 mmoles) of 1 M tetrabutylammonium fluoride in THF. The resulting mixture was stirred at ambient temperature for 4.5 hours.

The mixture was partitioned between ethyl acetate, ice-water, and aqueous sodium bicarbonate solution.

The organic phase was separated, washed with brine, dried over sodium sulfate, filtered, and evaporated.

Purification by silica gel chromatography using ethyl acetate-hexane (3:2) gave 1.65 g (80%) of 12.

IR (CH$_2$Cl$_2$) 3600, 2310, 1745, 1695, 1620 cm$^{-1}$.

EXAMPLE 24

Preparation of Carbapenem 13

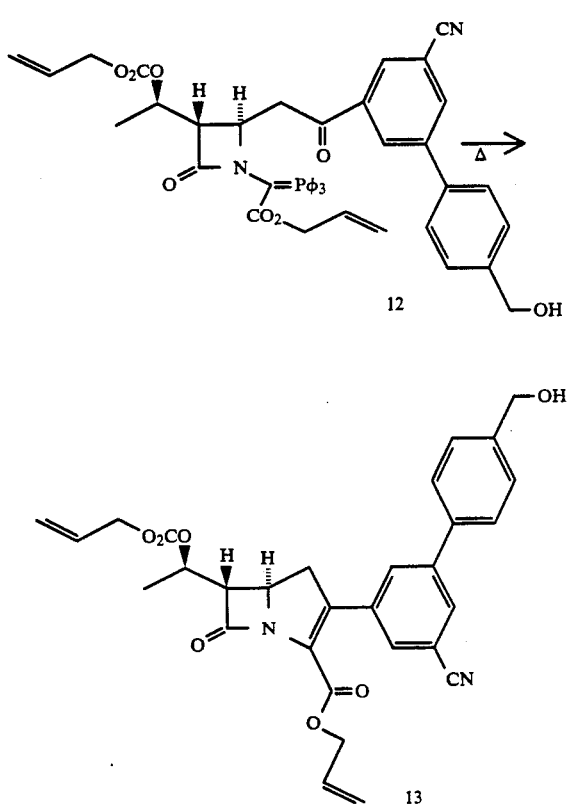

A stirred solution of 748 mg (0.93 mmoles) of phosphorane 12 in 30 mL of p-xylenes with a crystal of hydroquinone was heated at reflux under nitrogen for one hour. The cooled mixture was concentrated in vacuo and purified by plate layer chromatography using ethyl acetate-hexane (3:2) to give 384 mg (78%) of foamy 13.

NMR(CDCl$_3$) δ: 1.5 (d, J=6.4Hz, 3H), 3.26–3.34 (m, 2H), 3.47 (dd, J=2.9, 8.2Hz, 1H), 4.34 (dt, J=2.9, 8.9Hz, 1H), 4.63–4.73 (m, 4H), 4.78 (s, 2H), 5.14–5.42 (m, 5H), 5.88 (m, 2H), 7.46–7.6 (m, 5H), 7.79–7.81 (m, 2H).

EXAMPLE 25

Preparation of Carbapenem 14 and 15

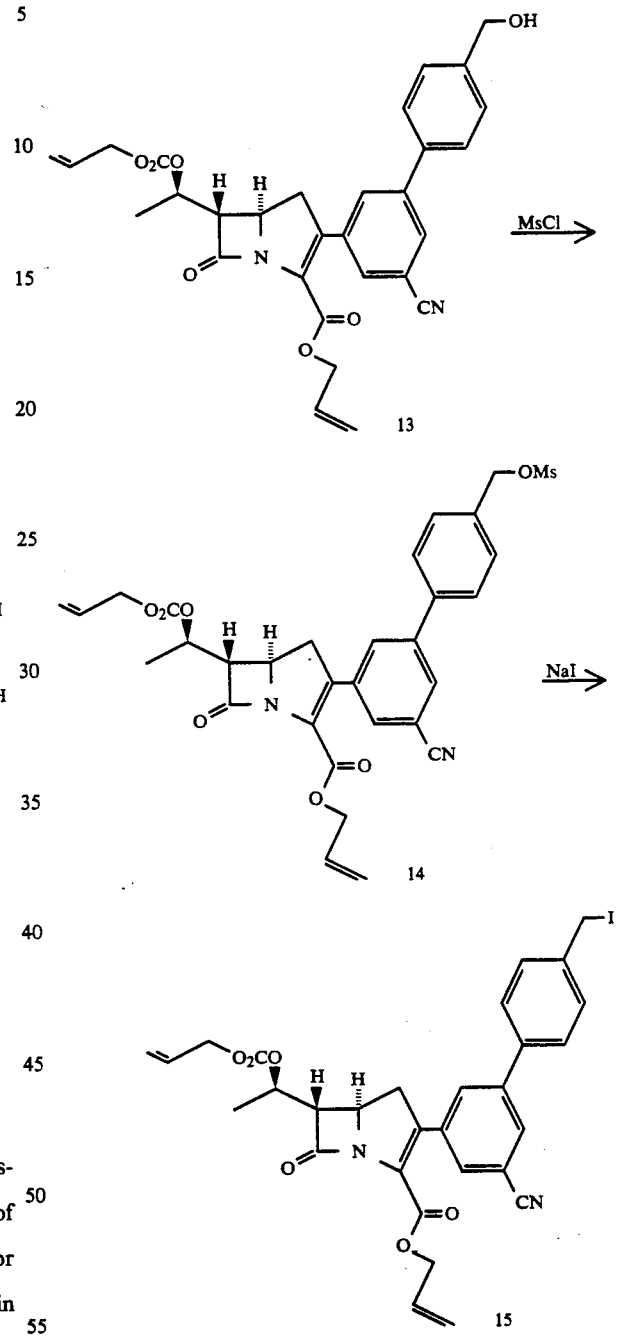

In a fashion analogous to Example 9, carbinol 13 was converted to the corresponding mesylate 14.

NMR(CDCl$_3$) δ: 1.53 (d, J=6Hz, 3H), 3.0 (s, 3H), 3.14–3.4 (m, 2H), 3.47 (dd, J=2.9, 8.9Hz, 1H), 4.34 (m, 1H), 4.63–4.8 (m, 4H), 5.14–5.42 (m, 5H), 5.30 (s, 2H), 5.8 (m, 2H), 7.51–7.62 (m, 5H), 7.81–7.82 (m, 2H).

Analogous to Example 10, mesylate 14 was converted to iodide 15.

NMR(CDCl$_3$) δ: 1.53 (d, J=6.4Hz), 3.25–3.40 (m, 2H), 3.47 (dd, J=2.9, 8.2Hz, 1H), 4.34 (m, 1H), 4.51 (s, 2H), 4.6–4.8 (m, 4H), 5.1–5.42 (m, 5H), 5.78–6.0 (m, 2H), 7.48–7.60 (m, 5H), 7.79–7.80 (m, 2H).

EXAMPLE 26

Preparation of Carbapenem 16

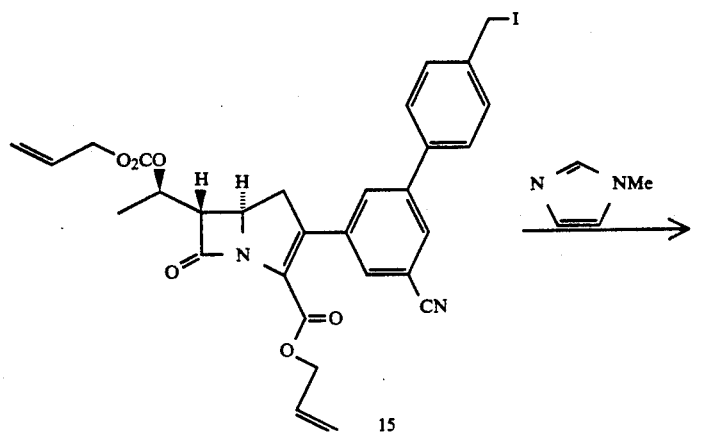

A mixture of 120 mg (0.188 mmoles) of iodide 15 and 29.9 μL (0.376 mmoles) of N-methylimidazole in 2 mL of sieve dried acetonitrile was stirred at ambient temperature overnight. The volatiles were removed under reduced pressure and the residue was taken up in a minimum amount of methylene chloride and the product 16 was precipitated by the addition of ether. Repetition of this procedure gave 76 mg (68%) of 16.

NMR(CDCl₃) δ: 1.53 (d, J=6.3Hz, 3H), 3.27–3.55

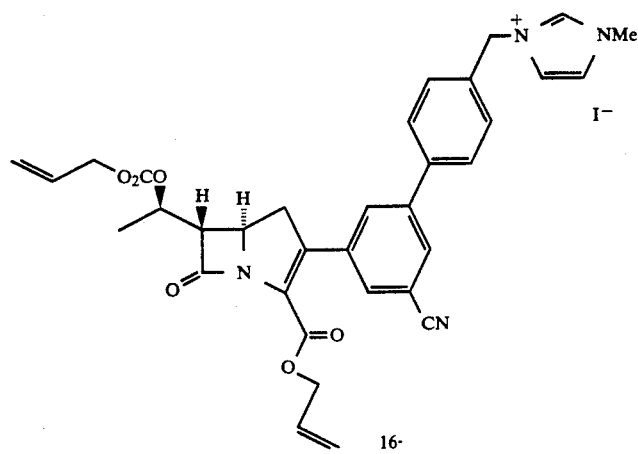

(m, 3H), 4.08 (s, 3H), 4.36 (m, 1H), 4.63–4.73 (m, 4H), 5.14–5.42 (m, 5H), 5.66 (s, 2H), 5.93 (m, 2H), 7.25–7.83 (m, 9H).

EXAMPLE 27

Preparation of Carbapenem 17

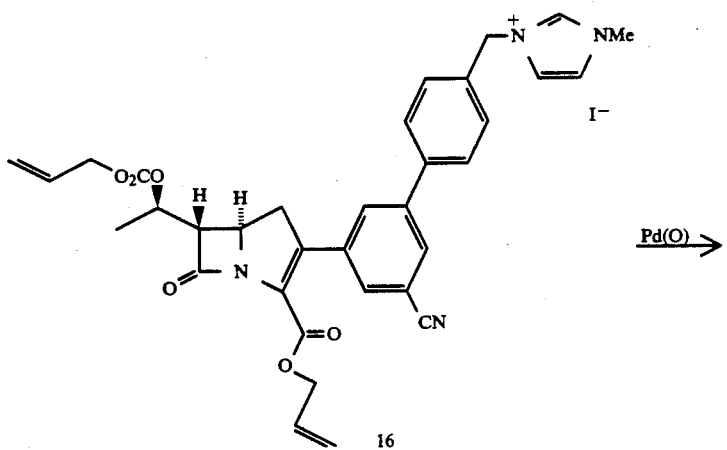

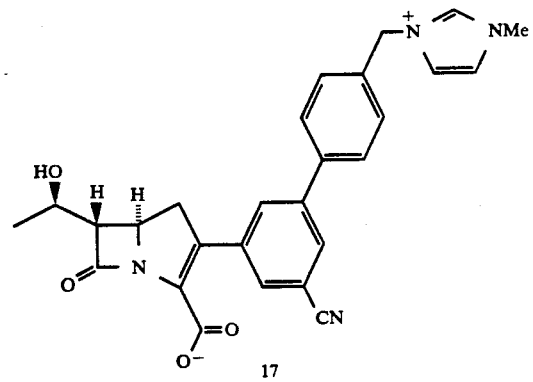

A mixture of 136 mg (0.23 mmoles) of carbapenem derivative 16, 35.9 mg (0.14 mmoles) of triphenylphosphine, 53.1 mg (0.05 mmoles) of tetrakistriphenylphosphine palladium, 36.1 μL (0.25 mmoles) of 2-ethylhexanoic acid, and 502 μL (0.25 mmoles) of 0.5 M potassium 2-ethylhexanoate in ethyl acetate was stirred at ambient temperature under nitrogen for 5 minutes and then at 0° C. for three hours. After this time, the precipitated product was triturated with ether and collected via centrifugation. Decantation of the supernatant, further washing with ether, and drying in vacuo provided crude 17. Purification by reverse phase plate layer chromatography in the cold using 30% THF in water provided, after extractive workup with acetonitrile-water (4:1) and freeze drying, 46 mg (43%) of pure 17.

IR (nuJol) 2230, 1755, 1590 cm$^{-1}$.

200 MHz NMR(D$_2$O-CD$_3$CN,3:1) δ: 1.62 (d, J=6.2Hz), 3.4–3.82 (m, 3H), 4.21 (s, 3H), 4.52–4.76 (m, 2H), 5.75 (s, 2H), 7.8–8.33 (m, 9H), 9.13 (bs, 1H). HDO 4.8.

UV (H$_2$O : λ$_{max}$ 305, 258 nm.

EXAMPLE 28

Preparation of N-2-carbamoylethylimidazole

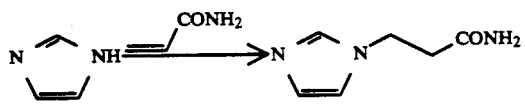

A stirred mixture of 3.4 g (49.9 mmoles) of imidazole, 3.55 g (49.9 mmoles) of acrylamide, and 7.6 g (49.9 mmoles) of 1,5-diazabicyclo[5.4.0]undec-5-ene (DBu) in 100 mL of sieve dried acetonitrile was heated at 80° C. under nitrogen for 2.0 hours. The mixture was let cool, where upon the product crystallized out of the solution.

The separated product was collected by suction filtration, washed well with cold acetonitrile-ether (1:1), and dried in vacuo to give 4.92 g (71%) of the title compound.

NMR(d$_4$-MeOH) δ: 2.68 (t, J=6.6Hz, 2H), 4.30 (t, J=6.6Hz, 2H), 4.87 (s, 2H), 6.93 (s, 1H), 7.1 (s, 1H), 7.63 (s, 1H).

EXAMPLE 29

Preparation of N-3-p-nitrobenzyloxycarbonyloxypropylimidazole

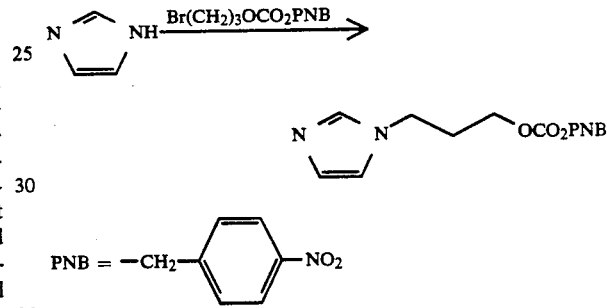

A Stilled mixture of 816.6 mg (1.2 mmoles) of imidazole and 954 mg (3.0 mmoles) of 3-p-nitrobenzyloxycarbonyloxypropylbromide in 10 mL sieve dried acetonitrile was refluxed under nitrogen for 5.0 hours.

The cooled mixture was partitioned between ethyl acetate, ice-water, and saturated, aqueous sodium bicarbonate solution and the organic phase was separated. It was washed with saturated sodium chloride solution, dried with sodium sulfate, filtered, and evaporated.

Purification by plate layer chromatography, eluted with ethyl acetate-methanol (10:1) gave 498 mg (43%) of the title compound.

NMR(CDCl$_3$) δ: 2.15 (p, J=6Hz, 2H), 4.08 (t, J=6.9Hz, 2H), 4.15 (t, J=6Hz, 2H), 5.25 (s, 2H), 6.9 (s, 1H), 7.07 (s, 1H), 7.48 (s, 1H), 7.56 (d, J=9Hz, 2H), 8.24 (d, J=9Hz, 2H).

Central to the instant invention was the safety benefit realized by the incorporation of the cyano group to the imidazoliummethylbiphenyl moiety of the carbapenem nucleus, as shown in Table II below. Quite unexpectedly, the antibiotics, produced by this incorporation, exhibit a greater margin of safety in a laboratory animal test model designed to predict the seizure potential of biologically active compounds. As indicated in Table II, the cyanobiphenylcarbapenems require four times as much to produce the same number of seizures exhibited by the analogous unsubstituted biphenylcarbapenems. This difference in activity was statistically significant and allows one to anticipate a much greater CNS safety profile for the compounds depicted.

TABLE II

INTRACISTERNAL ASSAY

TABLE II-continued

[Structure with OH, H, H stereochemistry on carbapenem core with CO2− and imidazolium-substituted biphenyl]

| R$^c$ | R' | CONVULSANT RESPONSE MCG/HEAD-ED$_{50}$ |
|---|---|---|
| —CH$_2$CH$_2$OH | —H | 35 |
| —CH$_2$CH$_2$OH | —CN | 100 |
| —CH$_3$ | —H | 35 |
| —CH$_3$ | —CN | 100 |
| —CH$_3$ | —Br | <12.5 |

The figure reported in Table II was the amount of active compound giving a 50% seizure rate in the rat, serving as a model for humans. For each compound, different concentrations were prepared in water and for each concentration, a group of animals were given an injection of 20 micro-liters into the intracisternal cavity. The seizure response of each member of the group was noted by observation.

What is claimed is:

1. Carbapenem compounds of the formula:

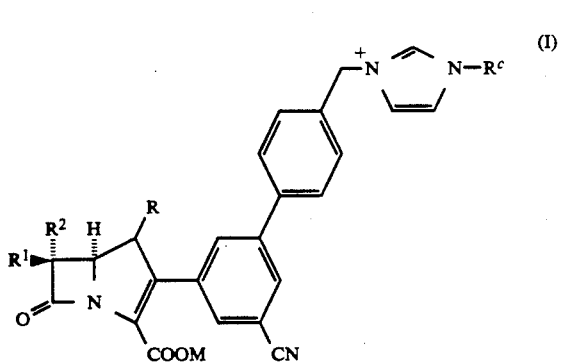

wherein:

R is H or CH$_3$;

R$^1$ and R$^2$ are independently H, CH$_3$—, CH$_3$CH$_2$—, (CH$_3$)$_2$CH—, HOCH$_2$—, CH$_3$CH(OH)—, (CH$_3$)$_2$C(OH)—, FCH$_2$CH(OH)—, F$_2$CHCH(OH)—, F$_3$CCH(OH)—, CH$_3$CH(F)—, CH$_3$CF$_2$—, or (CH$_3$)$_2$C(F)—;

R$^c$ is selected from the group consisting of —CF$_3$, and C$_{1-6}$ alkyl where the C$_{1-6}$ alkyl may be mono-substituted with a substituent selected from the group consisting of:

a) a trifluoromethyl group: —CF$_3$;
b) a halogen atom: —Br, —Cl, —F, or —I;
c) C$_1$-C$_4$ alkoxy radical: —OC$_{1-4}$ alkyl, wherein the alkyl is optionally mono-substituted by R$^q$, where R$^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$ and —COOC$_{1-4}$alkyl;

d) a hydroxy group: —OH;
e) a carbonyloxy radical: —O(C=O)R$^s$, where R$^s$ is C$_{1-4}$ alkyl or phenyl, each of which is optionally mono-substituted by R$^q$ as defined above;
f) a carbamoyloxy radical; —O(C=O)N(R$^y$)R$^z$ where R$^y$ and R$^z$ are independently H, C$_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$—, to form a ring (where the ring is optionally mono-substituted with R$^q$ as defined above);

g) a sulfur radical: —S(O)$_n$—R$^s$ where n=0–2, and R$^s$ is defined above;
h) a sulfamoyl group: —SO$_2$N(R$^y$)R$^z$ where R$^y$ and R$^z$ are as defined above;
i) azido; N$_3$
j) a formamido group: —N(R$^t$)(C=O)H, where R$^t$ is H or C$_{1-4}$ alkyl, and the alkyl thereof is optionally mono-substituted by R$^q$ as defined above;
k) a (C$_1$-C$_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;
l) a (C$_1$-C$_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;
m) a ureido group: —N(R$^t$)(C=O)N(R$^y$)R$^z$ where R$^t$, R$^y$ and R$^z$ are as defined above;
n) a sulfonamido group: —N(R$^t$)SO$_2$R$^s$, where R$^s$ and R$^t$ are as defined above;
o) a cyano group: —CN;
p) a formyl or acetalized formyl radical; —(C=O)H or —CH(OCH$_3$)$_2$;
q) (C$_1$-C$_4$ alkyl)carbonyl radical wherein the carbonyl is acetalized: —C(OCH$_3$)$_2$C$_{1-4}$ alkyl, where the alkyl is optionally mono-substituted by R$^q$ as defined above;
r) carbonyl radical: —(C=O)R$^s$, where R$^s$ is as defined above;
s) a hydroximinomethyl radical in which the oxygen or carbon atom is optionally substituted by a C$_1$-C$_4$ alkyl group: —(C=NOR$^z$)R$^y$ where R$^y$ and R$^z$ are as defined above, except they may not be joined together to form a ring;
t) a (C$_1$-C$_4$ alkoxy)carbonyl radical: —(C=O)OC$_1$-C$_4$ alkyl, where the alkyl is optionally mono-substituted by R$^q$ as defined above;
u) a carbamoyl radical: —(C=O)N(R$^y$)R$^z$ where R$^y$ and R$^z$ are as defined above;
v) an N-hydroxycarbamoyl or N(C$_1$-C$_4$ alkoxy)carbamoyl radical in which the nitrogen atom may be additionally substituted by a C$_1$-C$_4$ alkyl group; —(C=O)—N(OR$^y$)R$^z$ where R$^y$ and R$^z$ are as defined above, except they may not be joined together to form a ring;
w) a thiocarbamoyl group: —(C=S)N(R$^y$)(R$^z$) where R$^y$ and R$^z$ are as defined above;
x) thiocyanate: —SCN;
y) trifluoromethylthio: —SCF$_3$;
z) C$_5$-C$_7$ cycloalkyl group in which one of the carbon atoms in the ring is replaced by a heteroatom selected from O, S, NH or N(C₁-C₄ alkyl) and in which one additional carbon atom may be replaced by NH or N(C₁-C₄alkyl), and in which at least one carbon atom adjacent to each nitrogen heteroatom has both of its attached hydrogen atoms replaced by one oxygen thus forming a carbonyl moiety and there are one or two carbonyl moieties present in the ring;

aa) $C_2$-$C_4$ alkenyl radical;

ab) $C_2$-$C_4$ alkenyl radical;

ac) $C_2$-$C_4$ alkynyl radical;

ad) a 2-oxazolidinonyl moiety in which the point of attachment is the nitrogen atom of the oxazolidinone ring, the ring oxygen atom is optionally replaced by a heteroatom selected from —S— and >NR' (where R' is as defined above) and one of the saturated carbon atoms of the oxazolidinone ring is optionally mono-substituted by one of the substituents a) to ac) above;

M is selected from:

i) hydrogen;

ii) a pharmaceutically acceptable esterifying group or removable carboxyl protecting group;

iii) an alkali metal or other pharmaceutically acceptable cation; or iv) a negative charge.

2. The compound of claim 1 wherein $R^1$ is hydrogen and $R^2$ is (R)—CH₃CH(OH)—.

3. The compound of claim 1 wherein $R^c$ is selected from the group consisting of:

| | |
|---|---|
| —CF₃, | —CH₂CH₂NHCOCH₃, |
| —CH₂CH₂Cl, | —CH₂CH₂NHCOOCH₃, |
| —CH₂CH₂OCH₂CH₃, | —CH₂CH₂NHCONH₂, |
| —CH₂CH₂OCH₂CH₂OH, | —CH₂CH₂NHSO₂CH₃, |
| —CH₂CH₂OCOCH₃, | —CH₂CH₂CHO, |
| —CH₂CH₂OCO-phenyl, | —CH₂CH₂COphenyl, |
| —CH₂CH₂OCO-phenyl-p-OH, | —CH₂CH₂(C═NOH)H, |
| —CH₂CH₂OCONHCH₃, | —CH₂CH₂COOCH₃, |
| —CH₂CH₂SOCH₃, | —CH₂CH₂CON(OH)CH₃, |
| —CH₂CH₂SO₂CH₃, | —CH₂CH₂CSNH₂, |
| —CH₂CH₂SO₂NH₂, | —CH₂CH₂SCN, |
| —CH₂CH₂N₃, | —CH₂CH₂SCF₃, |
| —CH₂CH₂NHCHO, | —CH₂CH₂NH₂, and |
| —CH₂CH₂NCH₃CHO, and | —CH₂CH₂N(CH₃)₂. |

4. The compound of claim 1 wherein $R^c$ is selected from the group consisting of:

| | |
|---|---|
| —CH₃, | —CH₂CH₂CH₂OCONH₂, |
| —CH₂CH₂OH, | —CH₂CH₂CONH₂, |
| —CH₂CH₂CH₂OH, | —CH₂CH₂OCONH₂, |
| —CH₂CONH₂, | —CH₂CN, |
| —CH₂CH₂CH₂CONH₂, and | —CH₂CH₂CN. |

5. A compound of claim 1 and selected from the group consisting of:

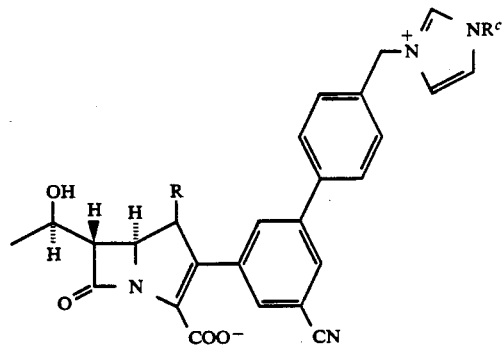

wherein
R is H or CH₃; and
Rc is selected from the group consisting of:

| | |
|---|---|
| —CH₃, | —CH₂CH₂CH₂OCONH₂ |
| —CH₂CH₂OH, | —CH₂CH₂CONH₂, |
| —CH₂CH₂CH₂OH, | —CH₂CH₂OCONH₂, |
| —CH₂CONH₂, | —CH₂CN, |
| —CH₂CH₂CH₂CONH₂, and | —CH₂CH₂CN. |

6. The compound of the formula:

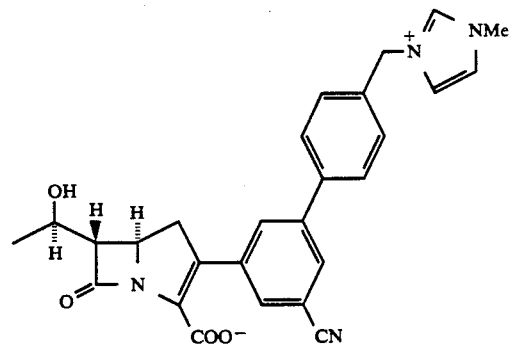

7. The compound of the formula:

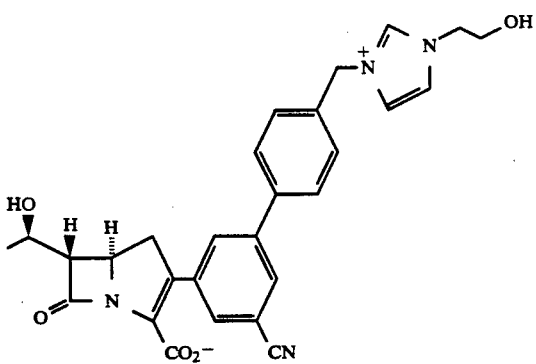

8. A composition comprising a pharmaceutically acceptable carrier and from 0.1% to about 99% by weight of active material of claim 1.

9. A composition according to claim 8 which further comprises an inhibitorily effective amount of a DHP inhibitor.

10. A composition according to claim 9 wherein said DHP inhibitor is 7-(L-2-amino-2-carboxyethylthio)-2-

(2,2-dimethylcyclopropanecarboxamide)-2-heptanoic acid.

11. A method for treating bacterial infection in mammals comprising administering a pharmaceutical composition comprising an effective amount of a compound of claim 1 and a pharmaceutically acceptable carrier therefor.

12. A method according to claim 11 which further comprises administering an inhibitorily effective amount of a DHP inhibitor.

13. A method according to claim 12 wherein said DHP inhibitor is 7-(L-2-amino-2-carboxyethylthio)-2-(2,2-dimethylcyclopropanecarboxamide)-2-heptanoic acid.

14. A compound of claim 1 having the formula:

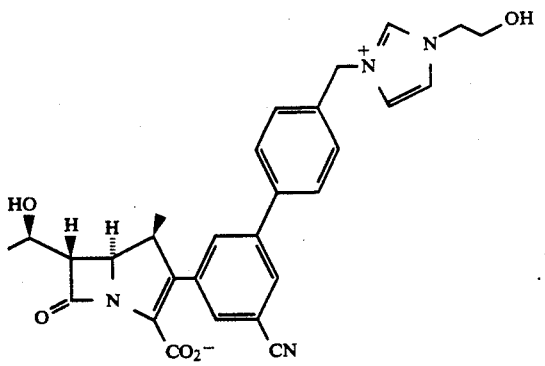

* * * * *